(12) United States Patent
Alt et al.

(10) Patent No.: US 7,838,503 B2
(45) Date of Patent: Nov. 23, 2010

(54) METHODS FOR EXTENDING THE REPLICATIVE LIFESPAN OF CELLS

(75) Inventors: Frederick W. Alt, Cambridge, MA (US); David B. Lombard, Cambridge, MA (US); Katrin F. Chua, Palo Alto, CA (US); Raul Mostoslavsky, Boston, MA (US); Hwei-Ling Cheng, Northborough, MA (US)

(73) Assignee: Children's Medical Center Corporation, Boston, MA (US)

( * ) Notice: Subject to any disclaimer, the term of this patent is extended or adjusted under 35 U.S.C. 154(b) by 412 days.

(21) Appl. No.: 11/453,283

(22) Filed: Jun. 14, 2006

(65) Prior Publication Data

US 2007/0160586 A1 Jul. 12, 2007

Related U.S. Application Data

(60) Provisional application No. 60/690,609, filed on Jun. 15, 2005.

(51) Int. Cl.
*C12Q 1/68* (2006.01)
*A61K 31/70* (2006.01)
*C07H 21/04* (2006.01)
*C07H 21/02* (2006.01)
*C12N 5/00* (2006.01)

(52) U.S. Cl. .............. 514/44 A; 435/375; 435/377; 435/6; 536/23.1; 536/24.1; 536/24.5

(58) Field of Classification Search ........... None
See application file for complete search history.

(56) References Cited

U.S. PATENT DOCUMENTS

| | | | |
|---|---|---|---|
| 4,690,915 A | 9/1987 | Rosenberg | |
| 5,126,132 A | 6/1992 | Rosenberg | |
| 5,443,983 A | 8/1995 | Ochoa et al. | |
| 5,766,920 A | 6/1998 | Babbitt et al. | |
| 5,846,827 A | 12/1998 | Celis et al. | |
| 6,040,177 A | 3/2000 | Riddell et al. | |
| 6,194,207 B1 | 2/2001 | Bell et al. | |
| 6,204,058 B1 | 3/2001 | Bolton | |
| 6,210,662 B1 | 4/2001 | Laus et al. | |
| 6,210,963 B1 | 4/2001 | Haddada et al. | |
| 6,225,044 B1 | 5/2001 | Klein et al. | |
| 6,227,368 B1 | 5/2001 | True | |
| 6,251,385 B1 | 6/2001 | Terman | |
| 6,255,073 B1 | 7/2001 | Cai et al. | |
| 6,787,300 B2 | 9/2004 | Guarente et al. | |
| 2001/0026930 A1 | 10/2001 | Guarente et al. | |
| 2003/0082597 A1 | 5/2003 | Cannon et al. | |
| 2003/0124101 A1 | 7/2003 | Gu et al. | |
| 2003/0157711 A1 | 8/2003 | Oh | |
| 2003/0175242 A1 | 9/2003 | Gruenberg | |
| 2003/0185790 A1 | 10/2003 | Bauer et al. | |
| 2003/0207325 A1 | 11/2003 | Guarente et al. | |
| 2004/0005574 A1 | 1/2004 | Guarente et al. | |
| 2004/0028607 A1 | 2/2004 | Verdin et al. | |
| 2004/0067228 A1 | 4/2004 | Denu et al. | |
| 2004/0091953 A1 | 5/2004 | Verdin et al. | |
| 2004/0259247 A1* | 12/2004 | Tuschl et al. ............... 435/375 |
| 2005/0019865 A1 | 1/2005 | Kihm et al. | |

FOREIGN PATENT DOCUMENTS

WO WO2006006171 * 1/2006

OTHER PUBLICATIONS

Milligan et al., Journal of Medicinal Chemistry vol. 36(14):1923-1937, 1993.*
Iwama et al., "Enhanced Self-Renewal of Hematopoietic Stem Cells Mediated by the Polycomb Gene Product Bmi-1," *Immunity* 21:843-851 (2004).
Mikula et al., "Immortalized $p19^{ARF}$ Null Hepatocytes Restore Liver Injury and Generate Hepatic Progenitors After Transplantation," *Hepatology* 39(3):628-634 (2004).

* cited by examiner

*Primary Examiner*—Sean R McGarry
(74) *Attorney, Agent, or Firm*—Nixon Peabody LLP

(57) ABSTRACT

The present invention is directed to methods for enhancing the replicative capacity of cells, by culturing the cells in the presence of an active agent or compound which inhibits SIRT1. One method provides expanding stem cells by culturing the cells in the presence of a SIRT1 inhibitor. The resulting cultured cells can be used for a variety of applications including cell-based therapies such as bone marrow transplants, gene therapies, tissue engineering, and in vitro organogenesis.

15 Claims, 23 Drawing Sheets

COLONY FORMATION IN SOFT AGAR

| | CONTROL | c-myc |
|---|---|---|
| WT-1 | − | − |
| WT-2 | − | − |
| WT-3 | − | − |
| S1KO-1 | − | − |
| S1KO-2 (3T3) | − | − |
| S1KO-3 (3T3) | − | − |
| p53-1 | − | +++ |
| p53-2 | − | +++ |

Q-FISH: SIRT1 AND WT MEFs (PASSAGE 20)

| MEF LINE | GENOTYPE | # METAPHASES (# CHROMOSOMES) | TOTAL STRUCTURAL ABERRATIONS (PER METAPHASE) | END-TO-END CHROMOSOMAL FUSIONS (PER METAPHASE) | SIGNAL-FREE ENDS/TELOMERES (%) |
|---|---|---|---|---|---|
| E9 | +/+ | 35 (2286) | 0.08 (1 dc, 1 CB, 1 fg) | 0/35 | 9/9144 (0.1%) |
| E5 | −/− | 38 (2748) | 0.07 (2 CB, 1 tl) | 0/38 | 10/10992 (0.09%) |
| E7 | −/− | 21 (1321) | 0.08 (2 dc) | 0/21 | 5/5284 (0.09%) |

CB, CHROMATID BREAK; fg, FRAGMENT; dc, DETACHED CENTROMERE; tl, TRANSLOCATION

METHODS FOR EXTENDING THE REPLICATIVE LIFESPAN OF CELLS

CROSS-REFERENCE TO RELATED APPLICATIONS

This application claims the benefit under 35 U.S.C. §119(e) of U.S. Provisional Patent Application No. 60/690,609 filed Jun. 15, 2005.

FIELD OF THE INVENTION

The present application is directed to methods for extending the replicative lifespan of cells from a mammalian tissue, preferably for the ex vivo expansion of stem cells or other cells for cell based therapies.

BACKGROUND OF THE INVENTION

Considerable attention has focused on the development of cell-based therapies. For example, one type of cell-based therapy includes removing cells or tissue from an individual, manipulating the tissue ex vivo, and returning the cells to the individual. Treatments include the use of lymphokine activated killer (LAK) cells (see U.S. Pat. No. 4,690,915 issued to Rosenberg), tumor infiltrating lymphocytes (TIL) cells (see U.S. Pat. No. 5,126,132 issued to Rosenberg), cytotoxic T-cells (see U.S. Pat. No. 6,255,073 issued to Cai, et al.; U.S. Pat. No. 5,846,827 issued to Celis, et al.), expanded tumor draining lymph node cells (see U.S. Pat. No. 6,251,385 issued to Terman), genetically transformed stem cells (see U.S. Pat. No. 6,225,044 issued to Klein, et al.), mononuclear phagocytes (see U.S. Pat. No. 6,210,963 issued to Haddada, et al.), lymphocytes (see U.S. Pat. No. 6,194,207 issued to Bell, et al.; U.S. Pat. No. 5,443,983 issued to Ochoa, et al.; U.S. Pat. No. 6,040,177 issued to Riddell, et al.; U.S. Pat. No. 5,766,920 issued to Babbitt, et al.), dendritic cells (see U.S. Pat. No. 6,210,662 issued to Laus, et al.), lymphocytes treated with oxidizing agents (see U.S. Pat. No. 6,204,058 issued to Bolton), and cellular vaccines (see U.S. Pat. No. 6,227,368 issued to Hiserodt, et al).

The U.S. Food and Drug Administration (FDA) refers to these therapies as "Somatic Cell and Gene Therapies". As defined by the FDA, a "somatic cell therapy product" can be one or more autologous (self), allogeneic (intra-species), or xenogeneic (inter-species) cell(s) that have been propagated, expanded, selected, pharmacologically treated, or otherwise altered in biological characteristics ex vivo to be administered to humans and applicable to the prevention, treatment, cure, diagnosis, or mitigation of disease or injuries. A "gene therapy product", as defined by the FDA, can be one or more products that contain genetic material which are administered to modify and/or manipulate expression of genetic material and/or to alter biological properties of living cells.

The gap between the need for replacement of damaged or diseased organs in patients, with otherwise significant life-expectancy, and the supply of donor organs is growing at an ever increasing rate (Gridelli and Remuzzi, 2000). Tissue bioengineering and in vitro organogenesis research have the potential to bridge this gap. The availability of stem cells for organs in demand would greatly accelerate progress in these efforts.

A major obstacle to cell-based therapies is the availability of sufficient numbers of the desired cell type. Even in instances where it is possible to select for relatively purer populations such as hematopoietic stem cells (for example by cell sorting), these populations typically do not expand when cultured.

Accordingly, methods to expand cells ex vivo, particularly without significant alteration, are highly desirable. The ability to expand populations of cells, including a variety of stem cells as well as adult cells such as fibroblasts, beta cells, and cells of the immune system, would greatly contribute to cell-based therapies such as bone marrow transplants, gene therapies, tissue engineering, and in vitro organogenesis. Production of autologous stem cells to replace injured tissue would also reduce the need for immune suppression interventions. Considerable difficulty in achieving this objective has been encountered, thus far.

Thus, despite the need for methods to expand cells from an individual, including methods to expand them ex vivo, it has not been possible to readily do so.

SUMMARY OF THE INVENTION

The present invention is directed to methods for enhancing the replicative capacity of cells, by culturing the cells in the presence of an active agent or compound which inhibits SIRT1. One embodiment of the invention provides expanding stem cells or other cells by culturing the cells in the presence of a SIRT1 inhibitor. The resulting cultured cells can be used for a variety of applications including cell-based therapies such as bone marrow transplants, gene therapies, tissue engineering, and in vitro organogenesis.

The present invention provides a method of increasing the replicative capacity of mammalian cells, comprising culturing the cells in the presence of an active agent or compound which inhibits SIRT1.

Any compound or agent which inhibits SIRT1 can be used in the methods of the invention. In one embodiment, the agent inhibits the activity of the SIRT1. In another embodiment, the agent or compound inhibits SIRT1 by decreasing transcription. Preferred inhibitors include DNA, RNA, an RNA interfering agent, PNA, a small organic molecule, a natural product, a protein, an antibody, a peptide and a peptidomimetic.

In one particularly preferred method, SIRT1 is inhibited by decreasing transcription by an RNA interfering agent which is a double-stranded, short interfering RNA (siRNA). Preferably, the siRNA is about 15 to about 28 nucleotides in length. Even more preferably, the siRNA is about 19 to about 25 nucleotides in length. The siRNA is about 21 nucleotides in length. In one embodiment, the siRNA is double-stranded and comprises a 3' overhand on each strand. Preferably, the siRNA inhibits SIRT1 by transcriptional silencing.

The methods of the present invention can be used to enhance the replicative lifespan of any cells which can divide in culture. The methods of the present invention can be used to increase the replicative lifespan of any cells for which it is desirable to expand cells in vitro, including stem cells and non-stem cells. Preferred cells include embryonic stem cells, somatic stem cells, umbilical cord blood stem cells, unrestricted somatic stem cells (USSC) derived from human umbilical cord blood, mesenchymal stem cells, mesenchymal progenitor cells, hematopoietic stem cells, hematopoietic lineage progenitor cells, neural stem cells, neural progenitor cells, endothelial stem cells, endothelial progenitor cells, and fibroblasts. Preferred somatic stem cells include bone marrow derived stem cells, adipose derived stem cells, mesenchymal stem cells, neural stem cells, liver stem cells, hepatocyte precursor cells, pancreatic stem cells, skin stem cells, and corneal epithelium stem cells.

In one preferred embodiment, the cells are human cells. In another preferred embodiment, the cells are murine cells.

The methods of the present invention enhance the replicative lifespan of the cells cultured in the presence of the SIRT1 inhibitor, resulting in their extended expansion in vitro. Preferably, the cultured cells undergo at least one mitotic cell division. Even more preferably, the cultured cells undergo at least ten mitotic cell divisions.

In one preferred embodiment, the cultured cells are capable of self-renewal and expansion in culture, and have the potential to differentiate into cells of other phenotypes.

One embodiment of the present invention provides cells obtained by culturing cells in the presence of a SIRT1 inhibitor.

The present invention also provides methods of treating a patient in need of a cell-based therapy, by selecting a patient in need of a cell-based therapy; removing cells from said patient or donor; culturing the cells under conditions which inhibit SIRT1; harvesting the cultured cells; and transplanting the cultured cells into the patient.

One embodiment of the invention provides a method of gene therapy, by a) selecting a patient in need of gene therapy; removing cells from the patient or donor; culturing the cells under conditions which inhibit SIRT1; transducing DNA into said cultured cells; harvesting said cultured cells; and transplanting said cultured cells into said patient.

Yet another embodiment of the invention provides methods for screening for a compound or agent useful for increasing the replicative lifespan of cells, by screening a library of candidate compounds to identify those compounds which inhibit SIRT1.

BRIEF DESCRIPTION OF THE DRAWINGS

FIG. 1A shows numbers of population doublings (PD) over serial passaging according to a 3T3 protocol, carried out in triplicate for two independent WT and S1KO cell lines. The data is representative of 6 independent experiments, and for MEFs derived from multiple mouse litters, and from two independent gene-targeted disruptions of SIRT1 function (Cheng et al., 2003). FIG. 1B shows colony formation upon seeding at low density ($10^3$ cells/10 cm plate). Quantitation of the average number of colonies from three independent experiments is indicated. In all panels, error bars indicate the standard error of the mean. FIGS. 1C and 1D show acute inactivation of SIRT1 in conditionally targeted MEFs by Adenoviral Cre recombinase extends replicative lifespan. FIG. 1C shows Southern and Western analysis of Cre-deletion in $ex4^{Flox}$/S1KO MEFs, following treatment with Adenoviral GFP-Cre or control GFP. For Southern analysis, genomic DNA genomic DNA was digested with Bgl II and probed with an internal Eco RI-Sal I fragment (Cheng et al., 2003). Bands corresponding to non-deleted ($ex4^{Flox}$) and deleted ($\Delta ex4$) conditional-targeted allele are indicated. In this Southern, the S1KO null allele results in a 3.4 kb band. For Western analysis, the wild-type (wt) and mutant ($\Delta ex4$) SIRT1 proteins are indicated. FIG. 1D shows 3T3 serial passaging assays, in triplicate, of $ex4^{Flox}$/S1KO and $ex4^{Flox}$/WT lines following GFP-Cre deletion or control GFP treatment. FIGS. 1E and F show reintroduction of exogenous SIRT1 into late passage S1KO MEF cultures. FIG. 1E shows Western analysis of SIRT1 protein levels following reconstitution with SIRT1 (S1) or control (Co) virus, compared to endogenous levels (WT). FIG. 1F shows serial passaging according to 3T3 protocol as in FIG. 1. Arrow indicates retroviral transduction with SIRT1 or empty virus control at passage 7.

In FIG. 2A, Western analysis of $p19^{ARF}$, p53, and acetylated p53 levels is shown in passage 3 MEFs, at base-line or following treatment with 0.2 ug/ml Adriamycin for 8 hours. FIG. 2B shows Western analysis of $p19^{ARF}$, p53 and acetylated p53 levels in S1KO and WT control MEFs at passages 2, 5, and 8. FIG. 2C shows reversal of $p19^{ARF}$ levels upon reconstitution with exogenous SIRT1 at passage 7. FIG. 2D shows Western analysis of $p19^{ARF}$ levels in SIRT1-, p53-doubly deficient MEFs. In all panels, error bars indicate the standard error of the mean.

FIG. 3A shows cell-cycle arrest (S-phase ratio, calculated as ratio of BrdU incorporation in treated cells compared to untreated cells) was measured 18 hours after exposure of cultures to the indicated doses of $H_2O_2$. Data represent the mean of three independent cell lines. FIG. 3B shows proliferation of cells cultured in sub-lethal concentrations of $H_2O_2$ (50 uM), or under low serum (3%). FIGS. 3C and D show senescence-associated beta-galactosidase activity of cells treated as in FIG. 3B. FIG. 3E shows levels of $p19^{ARF}$ in cells treated as in FIG. 3B. Co, control; LS, low serum; HP, hydrogen peroxide. In all panels, error bars indicate the standard error of the mean.

FIG. 4A shows cell-cycle arrest following exposure to oncogenic Ras. S-phase ratio indicates the ratio of S-phase cells in $H-Ras^{V12}$-treated cells compared to control-treated cells. Data represent average of three independent experiments. WT3T3 indicates immortalized, late passage WT lines. FIG. 4B shows representative soft agar assays of passage 6 (P6) and passage 50 (P50) passage S1KO and WT MEF lines after infection with $H-Ras^{V12}$. Experiments were carried out in triplicate. Average number of colonies following Ras treatment were as follows: two independent early passage WT lines: 0.3±0.6; three independent S1KO lines: 0.3±0.6; late passage 3T3 lines derived from WT MEFs: 21.7±10, 24±7, 23±5; late passage 3T3 lines derived from KO MEFs: 0.3±0.6, 0.3±0.6, 0; NIH3T3 cells: 34.3±6.7. FIG. 4C shows Western analysis of $p19^{ARF}$ and p21 protein induction following infection with retroviral $H-Ras^{V12}$ (+) or control virus (−) in WT3T3 and S1KO3T3 lines, derived from serial passaging according to 3T3 protocols. In all panels, error bars indicate the standard error of the mean.

FIGS. 6A-B show 3T3 serial passaging assays of conditional SIRT1 MEFs as in FIG. 2. FIG. 6A shows $ex4^{Flox}$/S1KO and $ex4^{Flox}$/WT lines (different than in FIG. 1) following Cre deletion or control GFP treatment, carried out in triplicate. FIG. 6B shows average of 5 independent $ex4^{Flox}$/S1KO and 2 independent $ex4^{Flox}$/WT lines. FIG. 6C shows colony formation assays of 5 independent $ex4^{Flox}$/S1KO and 2 independent $ex4^{Flox}$/WT MEF lines, following GFP-Cre deletion or GFP control treatment. Experiments were carried out in triplicate for each MEF line FIG. 6D shows serial passaging of a second independent late passage S1KO MEF line following reconstitution with retroviral SIRT1 at passage 7 (arrow). FIG. 6E shows proliferation curves of SIRT1KO MEFs reconstituted with recombinant WT (SIRT1WT) or mutant SIRT1 (SIRT1HY) retrovirus at passage 5. Uninfected S1KO and WT MEFs are shown for comparison. The data represent the average of three independent experiments. Following selection for retrovirus, cells were seeded at $10^6$ per well of 6-well plates, and harvested and counted each day. Cell numbers were normalized to day 1. FIG. 6F shows colony formation assays of four late passage S1KO lines following reconstitution with retroviral SIRT1 or empty virus control. p53-deficient MEFs and NIH3T3 lines are shown for comparison. In all panels, error bars represent the standard error of the mean.

FIG. 8A show levels of reactive oxygen species in cultures shown in FIG. 3, grown under low serum (3%) or sub-lethal concentrations of $H_2O_2$ (50 uM), measured by DCFDA fluorescence. Values represent mean fluorescence of three independent S1KO or WT MEF lines, and are normalized to control cultures. FIG. 8B shows increased levels of 8-oxoguanine in cultures shown in (FIG. 8A), measured by flow cytometry. Values represent mean fluorescence, and are normalized to control cultures. FIG. 8C shows levels of reactive oxygen species measured by DCFDA fluorescence, following exposure to H-Ras$^{V12}$, as shown in FIG. 4. In FIG. 8A and FIG. 8C, ROS levels were measured using the probe DCFDA (5-chloromethyl-2',7'-dichlorodihydrofluorescein diacetate, acetyl ester), according to the manufacturer's instructions (Molecular Probes). Briefly, cells were incubated with 0.1 uM DCFDA for 1 hour, harvested, and DCFDA mean fluorescence measured by flow cytometry. In FIG. 8B, levels of 8-oxoguanine, were measured using the OxyDNA fluorometric assay kit (Calbiochem), and assayed by flow cytometry.

FIG. 9A shows proliferative arrest induced by retroviral expression of p19$^{ARF}$. FIG. 9B shows proliferative arrest induced by retroviral expression of p16$^{INK4A}$. FIG. 9C shows sample soft agar assays of primary WT MEFs, late passage S1KO MEFs, and p53-deficient MEFs following expression of retroviral c-myc (gift of Dr. William Hahn). FIG. 9D show summary of soft agar assays of the indicated MEF lines following transduction with c-myc or control retrovirus.

FIGS. 10A-D show genomic stability and telomere function. FIG. 10A shows metaphase chromosome spreads and genomic instability assays. Chromosome spreads were obtained using standard protocols (Kaushal et al., 2003). Briefly, MEF cultures were held for 3 hours in media supplemented 100 ng/ml colcemid to arrest cells in metaphase. Cells were dissociated and incubated in 75 mM KCl for 12-15 minutes before fixation in 3:1 methanol:acetic acid overnight and preparation of slides. To assay for genomic instability, metaphase chromosome spreads were stained with 4'6'-diamidino-2-phenylindole hydrochloride (DAPI), photographed using a Nikon E800 microscope equipped with a CCD camera, and scored on the presence of structural chromosomal abnormalities. The data represent the average of three independent wild-type and S1KO MEF lines, and 20 metaphases per line. FIG. 10B shows measurement of telomere restriction fragment (TRF) length. P15 MEFs were embedded in agarose plugs (CleanCut Agarose, BioRad, Hercules, Calif.) and lysed in 2 mg/mL proteinase K at 50° C. overnight. After Mbo I digestion, restriction fragments were resolved at 6 V/cm$^2$ for 23 hr using a pulsed field electrophoresis chamber (CHEF Mapper, Biorad), blotted to a nylon membrane and hybridized with a $\gamma^{32}$P-labeled 800 bp telomere (TTAGGG (SEQ ID. NO:1)) probe (gift of T. de Lange, Rockefeller University, New York). FIG. 10C shows telomere fluorescence in situ hybridization (FISH). P20 MEFs were incubated in colcemid (KaryoMAX, GibcoBRL), swollen in 30 mM sodium citrate, fixed in methanol/acetic acid (3/1) and air dried on slides overnight. After pepsin digestion, slides were denatured at 80° C. for 3 min, hybridized with a Cy3-labeled PNA telomeric probe (Cy3-(TTAGGG)$_3$ (SEQ ID. NO:2); Applied Biosystems, Bedford, Mass.) in 70% formamide at RT for 2 hr, washed, dehydrated, and mounted in Vectashield with DAPI (Vector Laboratories, Burlingame, Calif.). Images were taken with a Nikon Eclipse microscope equipped with a CCD camera (Applied Spectral Imaging, Carlsbad, Calif.) and a 63× objective lens. ~30 metaphases of each genotype were scored for total structural aberrations (chromatid breaks, detached centromeres, translocations) and chromosomal aberrations involving telomeres, such as "signal-free ends", end-to-end chromosomal fusions, rings, or the presence of extrachromosomal telomeric DNA, as summarized in FIG. 10D.

DETAILED DESCRIPTION OF THE INVENTION

Figure 1A:
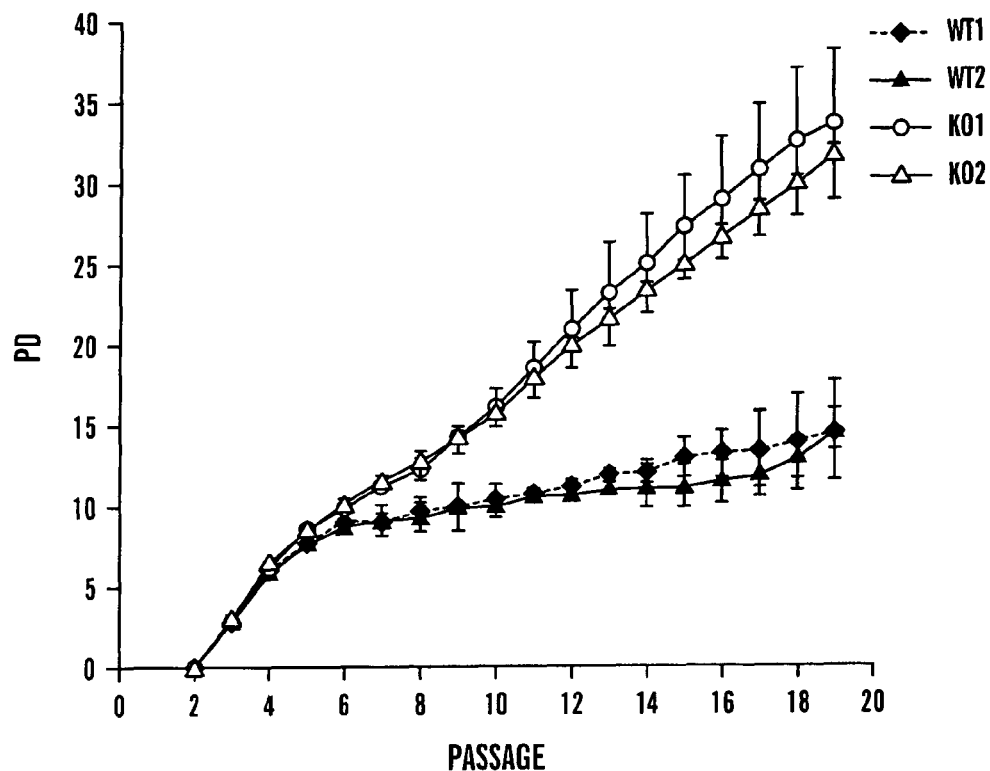
FIGS. 1A-1F show that S1KO MESS are resistant to culture-induced replicative senescence, and show impaired passage-induced accumulation of $p19^{ARF}$.

The invention relates to the discovery that mouse embryonic fibroblasts (MEFs) deficient for SIRT1, a mammalian Sir2 homolog, have dramatically increased resistance to replicative senescence. Extended replicative lifespan of SIRT1-deficient MEFs is associated with enhanced proliferative capacity under conditions of chronic, sublethal oxidative stress. Such SIRT1-deficient cells show normal p19ARF induction and cell-cycle arrest in response to DNA damage or oncogene expression. These results demonstrate that SIRT1 functions to promote replicative senescence.

Accordingly, the present invention provides methods to increase the replicative capacity of mammalian cells, by culturing cells in the presence of an effective amount of a compound or agent that suppresses the production or activity of SIRT1. Preferably, the compound interferes with the expression of the SIRT1 gene. Such compounds include, for example, siRNAs, antisense oligonucleotides, ribozymes, RNAi, and antibodies.

The expanded cultured cells of the invention can be used for a variety of applications, including cell-based therapies, sometimes referred to as cell replacement therapies, such as bone marrow transplants, gene therapies, tissue engineering, and in vitro organogenesis.

As used herein, the cells cultured in the presence of the SIRT1 inhibitor of the invention and expanded ex vivo are sometimes referred to as the cultured cells, or the expanded cells, or the expanded cultured cells.

Methods for Cell Expansion

Any compound or agent which inhibits SIRT1 can be used in the methods of the invention. In one embodiment, the agent inhibits the activity of the SIRT1. In another embodiment, the agent or compound inhibits SIRT1 by decreasing transcription. Preferred inhibitors include DNA, RNA, an RNA interfering agent, PNA, a small organic molecule, a natural product, a protein, an antibody, a peptide and a peptidomimetic.

Inhibition of SIRT1 Activity

One preferred embodiment of the invention provides a method for enhancing the replicative lifespan of cells by using an agent to inhibit SIRT1, wherein the agent or compound inhibits the activity of the SIRT1. This can be accomplished by a range of different approaches, including the use of antibodies, small molecules, and antagonists.

Any agent which inhibits the activity of SIRT1 can be used in the present invention. For example, one class of preferred compounds are sirtuin inhibitors, including but not limited to the sirtuin inhibitors disclosed in Grozinger et al., J. Biol. Chem. 42:38837-43 (2001), which is hereby incorporated by reference in its entirety. Preferred sirtuin inhibitors include the compounds A3, sirtinol, and M15 described therein. In one embodiment, sirtinol is a particularly preferred inhibitor.

Another preferred method of inhibiting SIRT1 provides a peptide which would competitively bind and thus inhibit SIRT1.

Further optimization of effective dosages can be determined empirically based on the specific tissue and cell type.

Downregulation of SIRT1

Preferably, SIRT1 expression may be inhibited ex vivo by the use of any method which results in decreased transcription of the gene encoding SIRT1. The sequence of the gene encoding mouse SIRT1 is available in Genbank asgenomic contig accession number NT 039495 (Mus musculus chromosome 10 genomic contig). The accession number for the gene encoding mouse SIRT1 is available in Genbank at NM_019812 (Mus musculus sirtuin 1). The sequence of the gene encoding human is available in Genbank as accession number NM 012238 (Homo sapiens sirtuin (silent mating type information regulation 2 homolog) 1), (SIRT1), mRNA; the DNA sequence of the human sequence from clone RP11-57G10 on chromosome 10 which includes the SIRT1 gene is available in Genbank as accession number AL133551.

In one preferred embodiment, RNAi technology can be used to inhibit or downregulate the expression of SIRT1 by decreasing transcription of the gene encoding SIRT1. RNA interference or "RNAi" is a term initially coined by Fire and co-workers to describe the observation that double-stranded RNA (dsRNA) can block gene expression when it is introduced into worms (Fire et al. (1998) Nature 391, 806-811). "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. See for example U.S. patent application Ser. Nos: 20030153519A1; 20030167490A1; and U.S. Pat. Nos. 6,506,559; 6,573,099, which are herein incorporated by reference in their entirety.

Isolated RNA molecules specific to SIRT1 mRNA, which mediate RNAi, are antagonists useful in the method of the present invention. In one embodiment, the RNA interfering agents used in the methods of the invention, e.g., the siRNAs used in the methods of the invention, can to be taken up actively by cells ex vivo by their addition to the culture medium, illustrating efficient delivery of the RNA interfering agents, e.g., the siRNAs used in the methods of the invention.

Other strategies for delivery of the RNA interfering agents, e.g., the siRNAs or shRNAs of used in the methods of the invention, may also be employed, such as, for example, delivery by a vector, e.g., a plasmid or viral vector, e.g., a lentiviral vector. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

The RNA interfering agents, e.g., the siRNAs of the invention, may be delivered singly, or in combination with other RNA interfering agents, e.g., siRNAs, such as, for example siRNAs directed to other cellular genes, e.g., apoptosis-related genes. The RNA interfering agents, e.g., siRNAs of the invention may also be administered in combination with other pharmaceutical agents which are used to treat or prevent cancer.

An "RNA interfering agent" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi). The target gene of the present invention is the gene encoding SIRT1.

As used herein, "inhibition of target gene expression" includes any decrease in expression or protein activity or level of the target gene or protein encoded by the target gene. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, 5, or 6 nucleotides. The length of the overhang is independent between the two strands, i.e., the length of the overhang on one strand is not dependent on the length of the overhang on the second strand. In one embodiment, the siRNA can inhibit SIRT1s by transcriptional silencing. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated be reference herein).

An siRNA may be substantially homologous to the target SIRT1 gene or genomic sequence, or a fragment thereof. As used herein, the term "homologous" is defined as being substantially identical, sufficiently complementary, or similar to the target mRNA, or a fragment thereof, to effect RNA interference of the target. In addition to native RNA molecules, RNAs suitable for inhibiting or interfering with the expression of a target sequence include RNA derivatives and analogs. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues may be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

SIRT1 expression may also be inhibited in vivo by the use of any method which results in decreased transcription of the gene encoding SIRT1. One embodiment uses antisense technology. Gene expression can be controlled through triple-helix formation or antisense DNA or RNA, both of which methods are based on binding of a polynucleotide to DNA or RNA. An antisense nucleic acid molecule which is complementary to a nucleic acid molecule encoding SIRT1 can be designed based upon the isolated nucleic acid molecules encoding SIRT1 by means known to those in the art.

Design and Preparation of siRNA Molecules

Synthetic siRNA molecules, including shRNA molecules, of the present invention can be obtained using a number of techniques known to those of skill in the art. One preferred siRNA is described in detail below in Example 1. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., an apoptosis-related gene or a cytokine, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide) (SEQ ID NO:3) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21) (SEQ ID NO:4), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

Delivery of RNA Interfering Agents

Methods of delivering RNA interfering agents, e.g., an siRNA of the present invention, or vectors containing an RNA interfering agent, e.g., an siRNA of the present invention, to the target cells, e.g., stem cells, for uptake include injection of a composition containing the RNA interfering agent, e.g., an siRNA, or directly contacting the cell, e.g., a stem cell, with a composition comprising an RNA interfering agent, e.g., an siRNA.

A viral-mediated delivery mechanism may also be employed to deliver siRNAs to cells in vitro and in vivo as described in Xia, H. et al. (2002) *Nat Biotechnol* 20(10): 1006). Plasmid- or viral-mediated delivery mechanisms of shRNA may also be employed to deliver shRNAs to cells in vitro and in vivo as described in Rubinson, D. A., et al. ((2003) *Nat. Genet.* 33:401-406) and Stewart, S. A., et al. ((2003) *RNA* 9:493-501). Other methods of introducing siRNA molecules of the present invention to target cells, e.g., tumor cells, include a variety of art-recognized techniques including, but not limited to, calcium phosphate or calcium chloride co-precipitation, DEAE-dextran-mediated transfection, lipofection, or electroporation as well as a number of commercially available transfection kits (e.g., OLIGOFECTAMINE® Reagent from Invitrogen) (see, e.g. Sui, G. et al. (2002) *Proc. Natl. Acad. Sci. USA* 99:5515-5520; Calegari, F. et al. (2002) *Proc. Natl. Acad. Sci., USA* Oct. 21, 2002; J-M Jacque, K. Triques and M. Stevenson (2002) *Nature* 418:435-437; and Elbashir, S. M et al. (2001) supra). Suitable methods for transfecting a target cell, e.g., a tubular cell of the kidney or a cardiac cell can also be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals. The efficiency of transfection may depend on a number of factors, including the cell type, the passage number, the confluency of the cells as well as the time and the manner of formation of siRNA- or shRNA-liposome complexes (e.g., inversion versus vortexing). These factors can be assessed and adjusted without undue experimentation by one with ordinary skill in the art.

The RNA interfering agents, e.g., the siRNAs or shRNAs of the invention, may be introduced along with components that perform one or more of the following activities: enhance uptake of the RNA interfering agents, e.g., siRNA, by the cell, e.g., tumor cells, inhibit annealing of single strands, stabilize single strands, or otherwise facilitate delivery to the target cell and increase inhibition of the target gene, SIRT1.

Cells

The methods of the present invention can be used to enhance the replicative lifespan of any cells which can be cultured. The methods of the present invention can be used to increase the replicative lifespan of any cells for which it is desirable to expand cells in vitro, including stem cells and non-stem cells. Preferred cells include embryonic stem cells, somatic stem cells, umbilical cord blood stem cells, unrestricted somatic stem cells (USSC) derived from human umbilical cord blood, postpartum-derived cells, mesenchymal stem cells, mesenchymal progenitor cells, hematopoietic lineage stem cells, hematopoietic lineage progenitor cells, neural stem cells, neural progenitor cells, endothelial stem cells, endothelial progenitor cells, and fibroblasts. Preferred somatic stem cells include bone marrow derived stem cells, adipose derived stem cells, mesenchymal stem cells, neural stem cells, liver stem cells, hepatocyte precursor cells, pancreatic stem cells, skin stem cells, and corneal epithelium stem cells.

One preferred embodiment of the invention provides methods to expand somatic stem cells from the skin, to generate new tissue for use in skin grafts. Another preferred embodiment of the invention provides methods to expand hematopoeitic stem cells or hair stem cells (Blainpain et al, 2004). Yet another preferred embodiment of the invention provides methods to expand hepatocytes and hepatocyte precursor cells (Mikula et al., 2004). The invention also provides methods to expand cartilage cells.

In one preferred embodiment, the cells are human cells. In another preferred embodiment, the cells are murine cells.

In one preferred embodiment, the cultured cells are capable of self-renewal and expansion in culture, and have the potential to differentiate into cells of other phenotypes.

In one aspect, the invention provides postpartum-derived cells (PPDCs) derived from postpartum tissue substantially free of blood. The PPDCs may be derived from placenta of a mammal including but not limited to human. The cells are capable of self-renewal and expansion in culture. The postpartum-derived cells have the potential to differentiate into cells of other phenotypes. The invention provides, in one of its several aspects cells that are derived from umbilical cord, as opposed to umbilical cord blood. The invention also provides, in one of its several aspects, cells that are derived from placental tissue.

In one embodiment, somatic tissue stem cells of the present invention include any stem cells isolated from adult tissue. Somatic stem cells include but are not limited to bone marrow derived stem cells, adipose derived stem cells, mesenchymal stem cells, neural stem cells, liver stem cells, and pancreatic stem cells. Bone marrow derived stem cells refers to all stem cells derived from bone marrow; these include but are not limited to mesenchymal stem cells, bone marrow stromal cells, and hematopoietic stem cells. Bone marrow stem cells are also known as mesenchymal stem cells or bone marrow stromal stem cells, or simply stromal cells or stem cells.

In certain embodiments, the stem cells act as precursor cells, which produce daughter cells that mature into differentiated cells. The stem cells can be isolated from the individual in need of stem cell therapy or from another individual. Preferably, the individual is a matched individual to insure that rejection problems do not occur. Therapies to avoid rejection of foreign cells are known in the art. Furthermore, somatic stem cells may be immune-privileged, so the graft versus host disease after allogenic transplant may be minimal or non-existent (Weissman, 2000). Endogenous or stem cells from a matched donor may be administered by any known means, preferably intravenous injection, or injection directly into the appropriate tissue.

In some embodiments, somatic tissue stem cells can be isolated from fresh bone marrow or adipose tissue by fractionation using fluorescence activated call sorting (FACS) with unique cell surface antigens to isolate specific subtypes of stem cells (such as bone marrow or adipose derived stem cells) for injection into recipients following expansion in vitro, as described above.

As stated above, cells may be derived from the individual to be treated or a matched donor. Those having ordinary skill in the art can readily identify matched donors using standard techniques and criteria.

Two preferred embodiments provide bone marrow or adipose tissue derived stem cells, which may be obtained by removing bone marrow cells or fat cells, from a donor, either self or matched, and placing the cells in a sterile container with a plastic surface or other appropriate surface that the cells come into contact with. The stromal cells will adhere to the plastic surface within 30 minutes to about 6 hours. After at least 30 minutes, preferably about four hours, the non-adhered cells may be removed and discarded. The adhered cells are stem cells, which are initially non-dividing. After about 2-4 days however the cells begin to proliferate.

Stem cells are undifferentiated cells defined by their ability at the single cell level to both self-renew and differentiate to produce progeny cells, including self-renewing progenitors, non-renewing progenitors and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent—able to give rise to all embryonic and extraembryonic cell types; (2) pluripotent—able to give rise to all embryonic cell types; (3) multipotent—able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood); (4) oligopotent—able to give rise to a more restricted subset of cell lineages than multipotent stem cells; and (5) unipotent—able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself and, under normal circumstances, differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated or differentiation-induced cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In a broad sense, a progenitor cell is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, cell that give rise to the lining of the intestine, and cells that give rise to pancreogenic and splanchogenic cells.

One preferred cell of the invention is postpartum-derived cells (PPDCs). Subsets of the cells of the present invention are referred to as placenta-derived cells (PDCs) or umbilical cord-derived cells (UDCs). PPDCs of the invention encompass undifferentiated and differentiation-induced cells. In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line).

Various terms are used to describe cells in culture. Cell culture refers generally to cells taken from a living organism and grown under controlled condition ("in culture"). A primary cell culture is a culture of cells, tissues or organs taken directly from organisms and before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged.

For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide.

Cell Culture Methods

The methods of the present invention enhance the replicative lifespan of the cells cultured in the presence of the SIRT1 inhibitor, resulting in their expansion in vitro. Preferably, the cultured cells undergo at least one mitotic cell division. Even more preferably, the cultured cells undergo at least ten mitotic cell divisions.

Cells can be obtained from donor tissue by dissociation of individual cells from the connecting extracellular matrix of the tissue. Tissue is removed using a sterile procedure, and the cells are dissociated using any method known in the art including treatment with enzymes such as trypsin, collagenase, and the like, or by using physical methods of dissociation such as with a blunt instrument.

Dissociation of cells can be carried out in any acceptable medium, including tissue culture medium. For example, a preferred medium for the dissociation of neural stem cells is low calcium artificial cerebrospinal fluid. The dissociated cells can be placed into any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. Serum can contain xanthine, hypoxanthine, or other compounds which enhance guanine nucleotide biosynthesis, although generally at levels below the effective concentration to suppress asymmetric cell kinetics. Thus, preferably a defined, serum-free culture medium is used, as serum contains unknown components (i.e. is undefined). A defined culture medium is also preferred if the cells are to be used for transplantation purposes. A particularly preferable culture medium is a defined culture medium comprising a mixture of DMEM, F12, and a defined hormone and salt mixture.

The culture medium can be supplemented with a proliferation-inducing growth factor(s). As used herein, the term "growth factor" refers to a protein, peptide or other molecule having a growth, proliferative, differentiative, or trophic effect on neural stem cells and/or neural stem cell progeny. Growth factors that may be used include any trophic factor that allows stem cells to proliferate, including any molecule that binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGF.alpha.), and combinations thereof. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGF.beta.s), insulin-like growth factor (IGF.sub.-1) and the like.

Cells can be cultured in suspension or on a fixed substrate. One particularly preferred substrate is a hydrogel, such as a peptide hydrogel, as described below. However, certain substrates tend to induce differentiation of certain cells. Thus, suspension cultures are preferable for such cell populations. Cell suspensions can be seeded in any receptacle capable of sustaining cells, particularly culture flasks, cultures plates, or roller bottles, more particularly in small culture flasks such as 25 cm$^2$ cultures flasks.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30.degree. C. to 40.degree. C. Cells are preferably cultured at temperatures between about 32.degree. C. to about 38.degree. C., and more preferably between about 35.degree. C. to about 37.degree. C.

Cells are preferably cultured for 3-30 days, preferably at least about 7 days, more preferably at least 10 days, still more preferably at least about 14 days. Cells can be cultured substantially longer. They can also be frozen using known methods such as cryopreservation, and thawed and used as needed.

Uses of Expanded Cultured Cells

The present invention also provides for the administration of expanded populations of cells to a patient in need thereof. The expanded cells of the present invention can be used for a variety of purposes, including but not limited to bone marrow transplants, gene therapies, tissue engineering, and in vitro organogenesis. Production of autologous cells to replace injured tissue would also reduce the need for immune suppression interventions.

Preferred tissues for the isolation and expansion of cells, for administration to a patient in need thereof, include but are not limited to the following: bone marrow, liver, lung, small intestine, colon, skin and cartilage such as from the knee.

One preferred embodiment of the invention provides administration of expanded skin cells to a patient in need thereof, including administration of new tissue for use in skin grafts. Another preferred embodiment of the invention provides administration of expanded hepatocytes to a patient in need thereof (Mikula et al, 2004). Yet another preferred embodiment of the invention provides administration of expanded cartilage cells to a patient in need thereof.

Yet another preferred embodiment of the invention provides administration of expanded hematopoeitic stem cells or hair stem cells (Blainpain et al, 2004).

Gene Therapy Applications

According to the invention, the cultured expanded cells can be further genetically altered prior to reintroducing the cells into the individual for gene therapy, to introduce a gene whose expression has therapeutic effect on the individual. Methods for introducing genes into the cultured cells are provided in detail below.

In some aspects of the invention, individuals can be treated by supplementing, augmenting and/or replacing defective and/or damaged cells with cells that express a therapeutic gene. The cells may be derived from cells of a normal matched donor or stem cells from the individual to be treated (i.e., autologous). By introducing normal genes in expressible form, individuals suffering from such a deficiency can be provided the means to compensate for genetic defects and eliminate, alleviate or reduce some or all of the symptoms.

Administration of Expanded Cultured Cells

This method involves administering by standard means, such as intravenous infusion or mucosal injection, the expanded cultured cells to a patient.

The discovery that cells may be expanded ex vivo and administered intravenously provides the means for systemic administration. For example, bone marrow-derived stem cells may be isolated with relative ease and the isolated cells may be cultured according to methods of the present invention to increase the number of cells available. Intravenous administration also affords ease, convenience and comfort at higher levels than other modes of administration. In certain applications, systemic administration by intravenous infusion is more effective overall. In a preferred embodiment, the stem cells are administered to an individual by infusion into the superior mesenteric artery or celiac artery. The cells may also be delivered locally by irrigation down the recipient's airway or by direct injection into the mucosa of the intestine.

After isolating the cells, the cells can cultured for a period of time sufficient to allow them to expand to desired numbers, without any loss of desired functional characteristics. For example cells can be cultured from 1 day to over a year. Preferably the cells are cultured for 3-30 days, more preferably 4-14 days, most preferably at least 7 days.

In one embodiment of the invention, the cultured cells can be induced to differentiate following expansion in vitro, prior to administration to the individual.

Differentiation of the cultured cells can be induced by any method known in the art which activates the cascade of biological events which lead to growth, which include the liberation of inositol triphosphate and intracellular $Ca.^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, MATRIGEL™ (Collaborative Research), and the like. Differentiation can also be induced by leaving the cells in suspension in the presence of a proliferation-inducing growth factor, without reinitiation of proliferation.

A preferred method for inducing differentiation of certain stem cells comprises culturing the cells on a fixed substrate in a culture medium that is free of the proliferation-inducing growth factor. After removal of the proliferation-inducing growth factor, the cells adhere to the substrate (e.g. poly-omithine-treated plastic or glass), flatten, and begin to differentiate into neurons and glial cells. At this stage the culture medium may contain serum such as 0.5-1.0% fetal bovine serum (FBS). However, for certain uses, if defined conditions are required, serum would not be used.

Differentiation can be determined using immunocytochemistry techniques well known in the art. Immunocytochemistry (e.g. dual-label immunofluorescence and immunoperoxidase methods) utilizes antibodies that detect cell proteins to distinguish the cellular characteristics or phenotypic properties of differentiated cell types compared to markers present on stem cells.

For administration of the cultured cells, the cells can be removed from culture dishes, washed with saline, centrifuged to a pellet and resuspended in a glucose solution which is infused into the patient.

Between $10^5$ and $10^{13}$ cells per 100 kg person are administered per infusion. Preferably, between about $1-5 \times 10^8$ and $1-5 \times 10^{12}$ cells are infused intravenously per 100 kg person. More preferably, between about $1 \times 10^9$ and $5 \times 10^{11}$ cells are infused intravenously per 100 kg person. For example, dosages such as $4 \times 10^9$ cells per 100 kg person and $2 \times 10^{11}$ cells can be infused per 100 kg person. The cells can also be injected directly into the intestinal mucosa through an endoscope.

In some embodiments, a single administration of cells is provided. In other embodiments, multiple administrations are used. Multiple administrations can be provided over periodic time periods such as an initial treatment regime of 3-7 consecutive days, and then repeated at other times.

The term "animal" here denotes all mammalian animals, including human. It also includes an individual animal in all stages of development, including embryonic and fetal stages. A "transgenic" animal is any animal containing cells that bear genetic information received, directly or indirectly, by deliberate genetic manipulation at the subcellular level, such as by microinjection or infection with recombinant virus.

The term treating (or treatment of) a condition refers to ameliorating the effects of, or delaying, halting or reversing the progress of, or delaying or preventing the onset of, a condition as defined herein.

The term effective amount refers to a concentration of a reagent or pharmaceutical composition, such as a growth factor, differentiation agent, trophic factor, cell population or other agent, that is effective for producing an intended result, including cell growth and/or differentiation in vitro or in vivo, or treatment of a bone or cartilage condition as described herein. With respect to growth factors, an effective amount may range from about 1 nanogram/milliliter to about 1 microgram/milliliter. With respect to cells as administered to a patient in vivo, an effective amount may range from as few as several hundred or fewer to as many as several million or more. In specific embodiments, an effective amount may range from 10.sup.3-10.sup.11. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term patient or subject refers to animals, including mammals, preferably humans, who are treated with the pharmaceutical compositions or in accordance with the methods described herein.

The term matrix as used herein refers to a support for the cells of the invention, for example, a scaffold (e.g., VICRYL, PCL/PGA, or RAD16) or supporting medium (e.g., hydrogel, extracellular membrane protein (e.g., MATRIGEL (BD Discovery Labware, Bedford, Mass.)).

The term pharmaceutically acceptable carrier (or medium), which may be used interchangeably with the term biologically compatible carrier or medium, refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or by breakdown and elimination through natural pathways.

Several terms are used herein with respect to cell-based therapies, also known as cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

Genetic Manipulation of Cultured Cells

In another embodiment of the invention, any gene(s) of interest can be introduced into the culture cells. As explained below, it is preferred that the genes are operably linked to an inducible promoter.

As used herein, the introduction of DNA into a host cell is referred to as transduction, sometimes also known as transfection or infection. Cultured cells, such as stem cells, can be transduced ex vivo at high efficiency.

As used herein, the terms "transgene", "heterologous gene", "exogenous genetic material", "exogenous gene" and "nucleotide sequence encoding the gene" are used interchangeably and meant to refer to genomic DNA, cDNA, synthetic DNA and RNA, mRNA and antisense DNA and RNA which is introduced into the cultured cell. The exogenous genetic material may be heterologous or an additional copy or copies of genetic material normally found in the individual or animal. When cells are to be used as a component of a pharmaceutical composition in a method for treating human diseases, conditions or disorders, the exogenous genetic material that is used to transform the cells may also encode proteins selected as therapeutics used to treat the individual and/or to make the cells more amenable to transplantation.

An expression cassette can be created for expression of the gene that leads to constitutive upregulation of guanine ribonucleotides. Such an expression cassette can include regulatory elements such as a promoter, an initiation codon, a stop codon, and a polyadenylation signal. It is necessary that these elements be operable in the cultured cells or in cells that arise from the cultured cells after infusion into an individual. Moreover, it is necessary that these elements be operably linked to the nucleotide sequence that encodes the protein such that the nucleotide sequence can be expressed in the cultured cells and thus the protein can be produced. Initiation codons and stop codons are generally considered to be part of a nucleotide sequence that encodes the protein.

A variety of promoters can be used for expression of the transgene. Promoters that can be used to express the gene are well known in the art. Promoters include cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter and the herpes simplex tk virus promoter. For example, one can use a tissue specific promoter, i.e. a promoter that functions in some tissues but not in others. Such promoters include EF2 responsive promoters, etc. Regulatable promoters are preferred. Such systems include those using the lac repressor from *E. coli* as a transcription modulator to regulate transcription from lac operator-bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-5551 (1992); Yao, F. et al., Human Gene Therapy, 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone or rapamycin [see Miller and Vvhelan, supra at FIG. 2]. Inducible systems are available from Invitrogen, Clontech and Ariad. Systems using a repressor with the operon are preferred. Regulation of transgene expression in target cells represents a critical aspect of gene therapy. For example, the lac repressor from *Escherichia coli* can function as a transcriptional modulator to regulate transcription from lac operator-bearing mammalian cell promoters [M. Brown et al., *Cell*, 49:603-612 (1987)]; Gossen and Bujard (1992); [M. Gossen et al., *Natl. Acad. Sci. USA*, 89:5547-5551 (1992)] combined the tetracycline repressor (tetR) with the transcription activator (VP16) to create a tetR-mammalian cell transcription activator fusion protein, tTa (tetR-VP16), with the teto-bearing minimal promoter derived from the human cytomegalovirus (hCMV) major immediate-early promoter to create a tetR-tet operator system to control gene expression in mammalian cells. Recently Yao and colleagues [F. Yao et al., *Human Gene Therapy*, supra] demonstrated that the tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter. One particular advantage of this tetracycline inducible switch is that it does not require the use of a tetracycline repressor-mammalian cells transactivator or repressor fusion protein, which in some instances can be toxic to cells [M. Gossen et al., *Natl. Acad. Sci. USA*, 89:5547-5551 (1992); P. Shockett et al., *Proc. Natl. Acad. Sci. USA*, 92:6522-6526 (1995)], to achieve its regulatable effects.

The effectiveness of some inducible promoters increases over time. In such cases one can enhance the effectiveness of such systems by inserting multiple repressors in tandem, e.g. TetR linked to a TetR by an IRES. Alternatively, one can wait at least 3 days before screening for the desired function. While some silencing may occur, it is minimized given the large number of cells being used, preferably at least $1 \times 10^4$, more preferably at least $1 \times 10^5$, still more preferably at least $1 \times 10^6$, and even more preferably at least $1 \times 10^7$, the effect of silencing is minimal. One can enhance expression of desired proteins by known means to enhance the effectiveness of this system. For example, using the Woodchuck Hepatitis Virus Posttranscriptional Regulatory Element (WPRE). See Loeb, V. E., et al., *Human Gene Therapy* 10:2295-2305 (1999); Zufferey, R., et al., *J. of Virol.* 73:2886-2892 (1999); Donello, J. E., et al., *J. of Virol.* 72:5085-5092 (1998).

Examples of polyadenylation signals useful to practice the present invention include but are not limited to human collagen I polyadenylation signal, human collagen II polyadenylation signal, and SV40 polyadenylation signal.

In order to maximize protein production, codons may be selected which are most efficiently translated in the cell. The skilled artisan can prepare such sequences using known techniques based upon the present disclosure.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene. These marker genes can be under the control of any promoter or an inducible promoter. These are well known in the art and include genes that change the sensitivity of a cell to a stimulus such as a nutrient, an antibiotic, etc. Genes include those for neo, puro, tk, multiple drug resistance (MDR), etc. Other genes express proteins that can readily be screened for such as green fluorescent protein (GFP), blue fluorescent protein (BFP), luciferase, LacZ, nerve growth factor receptor (NGFR), etc.

For example, one can set up systems to screen cultured cells automatically for the marker. In this way one can rapidly select transduced cultured cells from non-transformed cells. For example, the resultant particles can be contacted with about one million cells. Even at transduction rates of 10-15% one will obtain 100-150,000 cells. An automatic sorter that screens and selects cells displaying the marker, e.g. GFP, can be used in the present method.

Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Preferred vectors include viral vectors, fusion proteins and chemical conjugates. Retroviral vectors include Moloney murine leukemia viruses and pseudotyped lentiviral vectors such as FIV or HIV cores with a heterologous envelope. Other vectors include pox vectors such as orthopox or avipox vectors, herpesvirus vectors such as a herpes simplex I virus (HSV) vector (Geller, A. I. et al., (1995), *J. Neurochem*, 64: 487; Lim, F., et al., (1995) in *DNA Cloning: Mammalian Systems*, D. Glover, Ed., Oxford Univ. Press, Oxford England; Geller, A. I. et al. (1993), *Proc Natl. Acad. Sci.: U.S.A.* 90:7603; Geller, A. I., et al., (1990) *Proc Natl. Acad. Sci USA* 87:1149), adenovirus vectors (LeGal LaSalle et al. (1993), *Science*, 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The introduction of the gene into the cultured cells can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors, adjuvant-assisted DNA, gene gun, catheters, etc.

The vectors are used to transduce the cultured cells ex vivo. One can rapidly select the transduced cells by screening for the marker. Thereafter, one can take the transduced cells and grow them under the appropriate conditions or insert those cells into a host animal.

In one embodiment, the information to be introduced into the cell is preferably foreign to the species of animal to which the recipient belongs (i.e., "heterologous"), but the information may also be foreign only to the particular individual recipient, or genetic information already possessed by the recipient. In the last case, the introduced gene may be differently expressed than is the native gene.

Example

Mammalian SIRT1 Limits Replicative Lifespan in Response to Chronic Genotoxic Stress The *Saccharomyces cerevisiae* chromatin silencing factor Sir2 suppresses genomic instability and extends replicative lifespan. In contrast, we find that mouse embryonic fibroblasts (MEFs) deficient for SIRT1, a mammalian Sir2 homolog, have dramatically increased resistance to replicative senescence. Extended replicative lifespan of SIRT1-deficient MEFs correlates with enhanced proliferative capacity under conditions of chronic, sub-lethal oxidative stress. In this context, SIRT1-deficient cells fail to normally up-regulate either the p19$^{ARF}$ senescence-regulator or its downstream target p53. However, upon acute DNA damage or oncogene expression, SIRT1-deficient cells show normal p19$^{ARF}$ induction and cell-cycle arrest. Together, our findings demonstrate an unexpected SIRT1 function in promoting replicative senescence in response to chronic cellular stress and implicate p19$^{ARF}$ as a downstream effector in this pathway.

The *Saccharomyces cerevisiae* chromatin silencing factor Sir2 (Silent Information Regulator 2) is an NAD-dependent histone deacetylase that suppresses transcription at several genomic loci (Blander and Guarente, 2004). In addition, Sir2 suppresses recombination at the ribosomal DNA array, thereby extending yeast lifespan (Blander and Guarente, 2004; Kaeberlein et al., 1999; Sinclair and Guarente, 1997). Because of its NAD-dependence, the activity of Sir2 is linked to the energy status of the cell, providing a mechanism whereby cellular metabolism can influence lifespan. Overexpression or pharmacologic activation of Sir2 homologs in *Caenorhabditis elegans* and *Drosophila melanogaster* also extends lifespan (Astrom et al., 2003; Rogina and Helfand, 2004; Tissenbaum and Guarente, 2001; Wood et al., 2004). Seven mammalian Sir2 homologs, referred to as SIRT1-7, have been identified (Frye, 2000). Based on this conserved function in regulating lifespan in lower eukaryotes, mammalian Sir2 homologs have been proposed to play a similar role (Kaeberlein et al., 1999). As SIRT1 is a nuclear protein and is the mammalian homolog most highly related to Sir2, it has been the focus of a large body of recent studies.

SIRT1-deficient mice suffer multiple abnormalities, including defects in spermatogenesis and in heart and retina development (Cheng et al., 2003; McBurney et al., 2003). The highly pleiotrophic phenotype of SIRT1-deficient mice likely reflects the broad array of potential SIRT1 substrates (reviewed in (Blander and Guarente, 2004)). In some cells, SIRT1 inhibits apoptosis in response to genotoxic stress and may accomplish this by several mechanisms. SIRT1 deacetylates the p53 tumor suppressor protein (Cheng et al., 2003; Langley et al., 2002; Luo et al., 2001; Tissenbaum and Guarente, 2001; Vaziri et al., 2001), which down-regulates p53 via effects on stability and activity (Prives and Manley, 2001). SIRT1 also inhibits apoptosis and promotes DNA repair by deacetylating FOXO transcription factors (Brunet et al., 2004; Daitoku et al., 2004; Motta et al., 2004; Van Der Horst et al., 2004), and it inhibits Bax-induced apoptosis by deacetylating Ku70 (Cohen et al., 2004a). Expression of SIRT1 itself is activated by calorie restriction and acute nutrient withdrawal, and thus, may promote cellular adaptation to metabolic stress (Cohen et al., 2004b; Nemoto et al., 2004). As increased stress resistance is a frequent correlate of longevity in model organisms (Finkel and Holbrook, 2000), the ability of SIRT1 to modulate stress resistance in mammalian cells suggests a potential link with mammalian aging.

Cellular senescence has been employed as a model for mammalian aging (Campisi, 2000; Hayflick and Moorhead, 1961). This process, which can be induced by several stimuli, consists of a state of permanent cell-cycle arrest associated with characteristic changes in cell morphology. Human and mouse fibroblasts undergo a limited number of divisions in culture, eventually entering a state of cellular senescence known as replicative senescence (Campisi, 2000; Hayflick and Moorhead, 1961). In human fibroblasts, replicative senescence results from telomere attrition. In contrast, mouse embryonic fibroblasts (MEFs), which possess much longer telomeres than human cells, undergo replicative senescence as a result of sub-lethal oxidative damage incurred under standard culture conditions (Busuttil et al., 2004; Parrinello et al., 2003; Sherr and DePinho, 2000; Wright and Shay, 2000). Cellular senescence also may represent a tumor suppressor mechanism, preventing propagation of cells that incur potentially oncogenic mutations (Krtolica and Campisi, 2002). In this regard, a senescence-like state, termed premature senescence, is induced by introduction of activated oncogenes into primary fibroblasts (Serrano et al., 1997). Likewise, acute DNA damage in primary fibroblasts, as induced by various genotoxins, also triggers cellular senescence (Chen et al., 1995; Robles and Adami, 1998; Sedelnikova et al., 2004).

In MEFs, the p53 protein plays a critical role in promoting senescence via activation of a complex transcriptional program (Oren, 2003; Vousden and Lu, 2002). Activation of p53 by the p19$^{ARF}$ tumor suppressor protein promotes replicative senescence. In this case, oxidative stress triggers p19$^{ARF}$ induction, which positively regulates p53 via inhibition of MDM2, a protein that mediates p53 degradation (Kurokawa et al., 1999; Pomerantz et al., 1998; Zhang et al., 1998; Zindy et al., 1998). Consistent with the importance of the p19$^{ARF}$/p53 pathway in replicative senescence, spontaneous immortalization of MEFs during culture usually results from adaptive mutations in p53 or silencing of p19$^{ARF}$ (Kamijo et al., 1997; Sherr and DePinho, 2000). Like replicative senescence, premature senescence in response to activated oncogenes also is mediated by p19$^{ARF}$-dependent activation of p53 (Palmero et al., 1998). In this context, MEFs immortalized through mutations in the p19$^{ARF}$/p53 pathway are transformed, rather than growth arrested, by introduction of activated oncogenes (Kamijo et al., 1997; Serrano et al., 1997). Finally, cellular senescence induced by acute DNA damage also is mediated by p53, but via a pathway that is independent of p19$^{ARF}$ (Kamijo et al., 1997; Stott et al., 1998).

Potential roles of SIRT1 with respect to replicative senescence in mammalian cells have not been elucidated. However, certain findings have supported the notion that SIRT1, like yeast Sir2, might function to prevent senescence. In this regard, p53 is hyperacetylated in SIRT1-deficient MEFs (Cheng et al., 2003), and increased p53 acetylation has been associated with senescence (Pearson et al., 2000). Likewise, over-expression of SIRT1 inhibits oncogene-induced premature senescence in MEFs (Langley et al., 2002). On the other hand, total p53 protein levels are reduced in SIRT1-deficient MEFs (Cheng et al., 2003), an effect that could potentially inhibit senescence. Here, we have directly assessed the effect of SIRT1-deficiency on replicative senescence of MEFs. In marked contrast to Sir2 function in *S. cerevisiae*, we find that SIRT1 promotes replicative senescence in MEFs and that p19$^{ARF}$ is a novel downstream effector of SIRT1 in this pathway.

Results

SIRT1-Deficiency Abrogates Replicative Senescence.

Figure 1B:
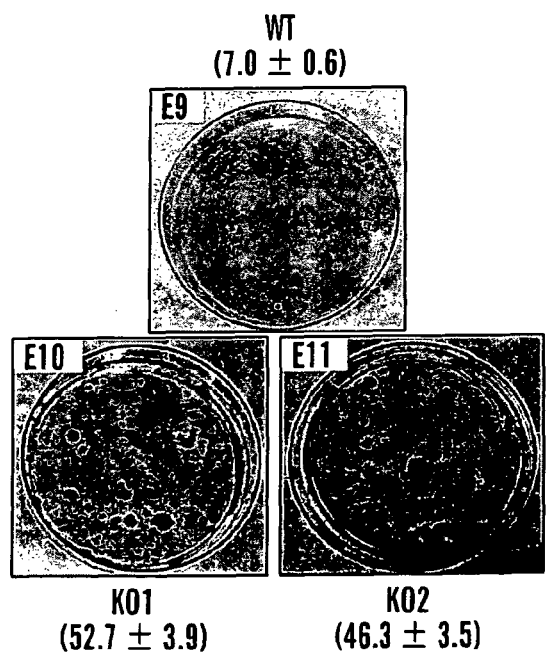

We have previously described SIRT1-deficient (referred to as S1KO) mice and S1KO MEFs (Cheng et al., 2003). To explore the role of SIRT1 in replicative senescence, we subjected S1KO and WT control MEFs to serial passage according to a 3T3 protocol (Todaro and Green, 1963). As previously shown, WT cultures underwent growth arrest after 5-8 passages (FIG. 1A) (Todaro and Green, 1963). Surprisingly, rather than arresting earlier than WT cells, S1KO cells did not undergo replicative senescence and continued to proliferate unabated (FIG. 1A). Similar results were obtained with 6 independent S1KO MEF lines (FIG. 1A, data not shown). The replicative capacity of MEFs can also be assessed by their ability to form colonies when seeded at low density. In this assay, WT MEF cultures underwent senescence before forming visible colonies, as previously described (Bardeesy et al., 2002; Sage et al., 2000), whereas S1KO MEF lines exhibited significantly greater clonogenic potential (FIG. 1B). Similar results were obtained for 4 independent S1KO and 3 independent WT MEF lines. Together, these observations suggest that SIRT1-deficiency extends, rather than shortens, the normal replicative lifespan of primary mouse fibroblasts.

Figure 1C:
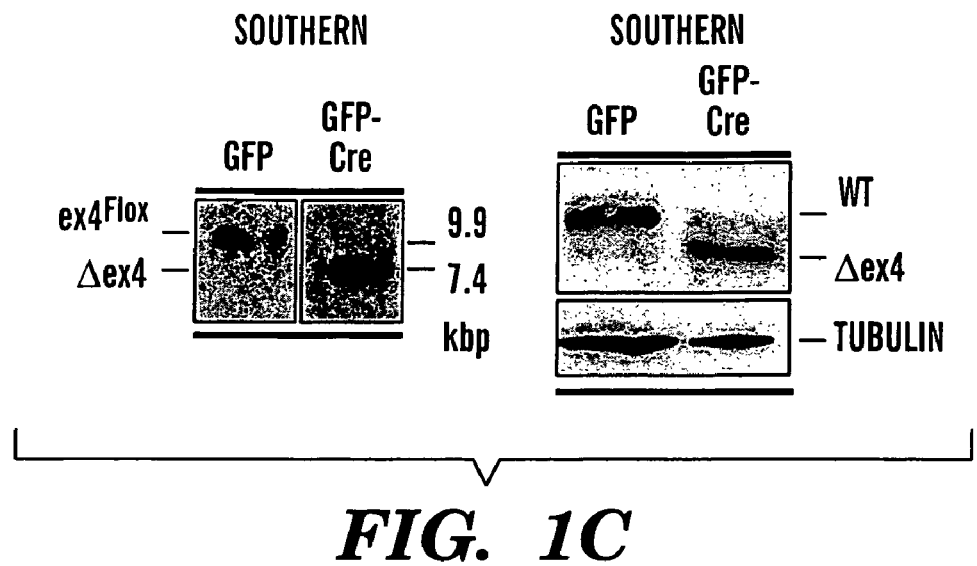
Figure 1D:
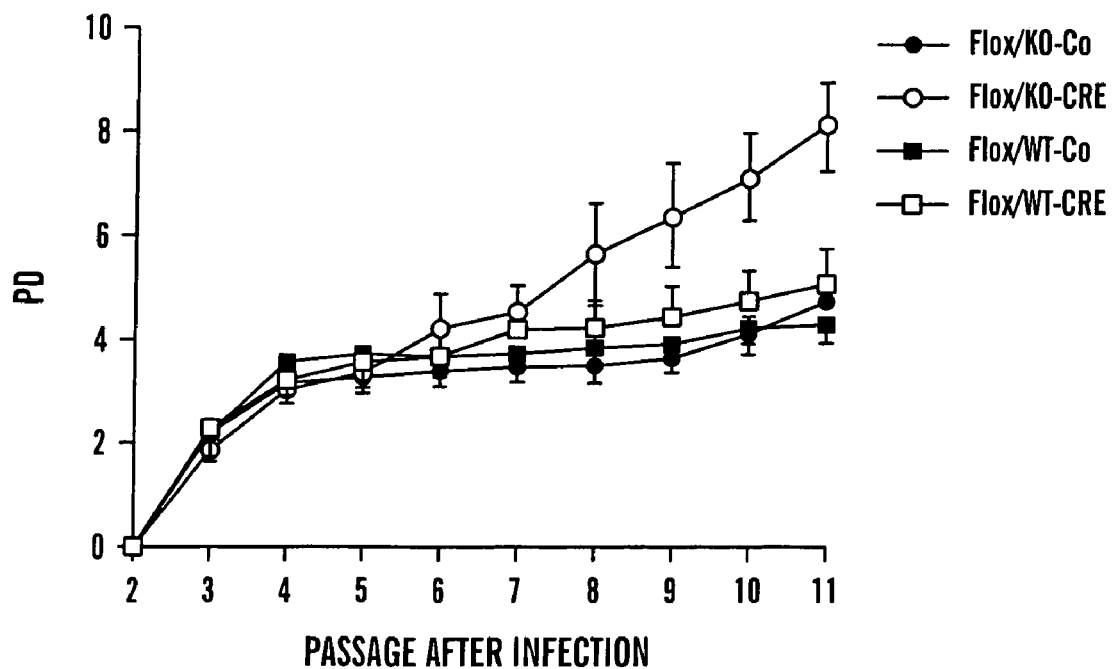
Figure 1E:
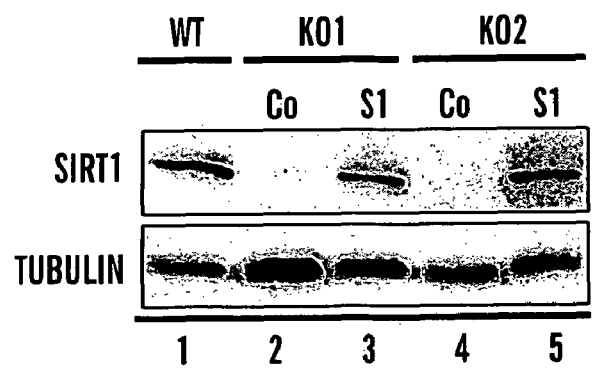

The increased replicative lifespan of SIRT1-deficient MEFs might be due to either an acute effect of SIRT1-deficiency or to secondary adaptations during growth of the S1KO cells in utero or in culture. To distinguish these possibilities, we acutely inactivated SIRT1 in cultured MEFs. We previously described mice in which exon 4 of SIRT1 was flanked by LoxP sites (ex4$^{Flox}$) and showed that mice harboring homozygous deletions of this exon were phenotypically indistinguishable from S1KO mice (Cheng et al., 2003). This finding indicates that the truncated SIRT1 protein generated by the exon 4 deletion allele is non-functional. Ex4$^{Flox}$/S1KO and ex4$^{Flox}$/WT MEF lines were generated from crosses of ex$_4^{Flox}$/ex$_4^{Flox}$ mice and mice heterozygous for the SIRT1 null allele (WT/S1KO). Adenoviral transduction of these MEFs with Cre Recombinase fused to Green Fluorescent Protein (GFP-Cre) resulted in nearly complete excision of floxed exon 4 and replacement of the full-length SIRT1 protein by the non-functional, faster-migrating Δex4 protein (FIG. 1C). 3T3 serial passage of multiple lines, following treatment with GFP-Cre or GFP control, demonstrated that the GFP-Cre-treated Δex4$^{Flox}$/S1KO cultures were strikingly resistant to replicative senescence, as compared to the same lines treated with GFP control virus or Δex4$^{Flox}$/WT MEFs treated with either GFP-Cre or GFP control virus (FIG. 1E). Similar results were obtained with 6 additional ex4$^{Flox}$/S1KO MEF lines and 3 additional ex4$^{Flox}$/WT MEFs lines, in either serial passage or colony formation experiments (FIG. 6). Thus, acute inactivation of SIRT1 in MEFs confers resistance to replicative senescence, demonstrating that this is a direct effect of loss of SIRT1 function.

Figure 1F:
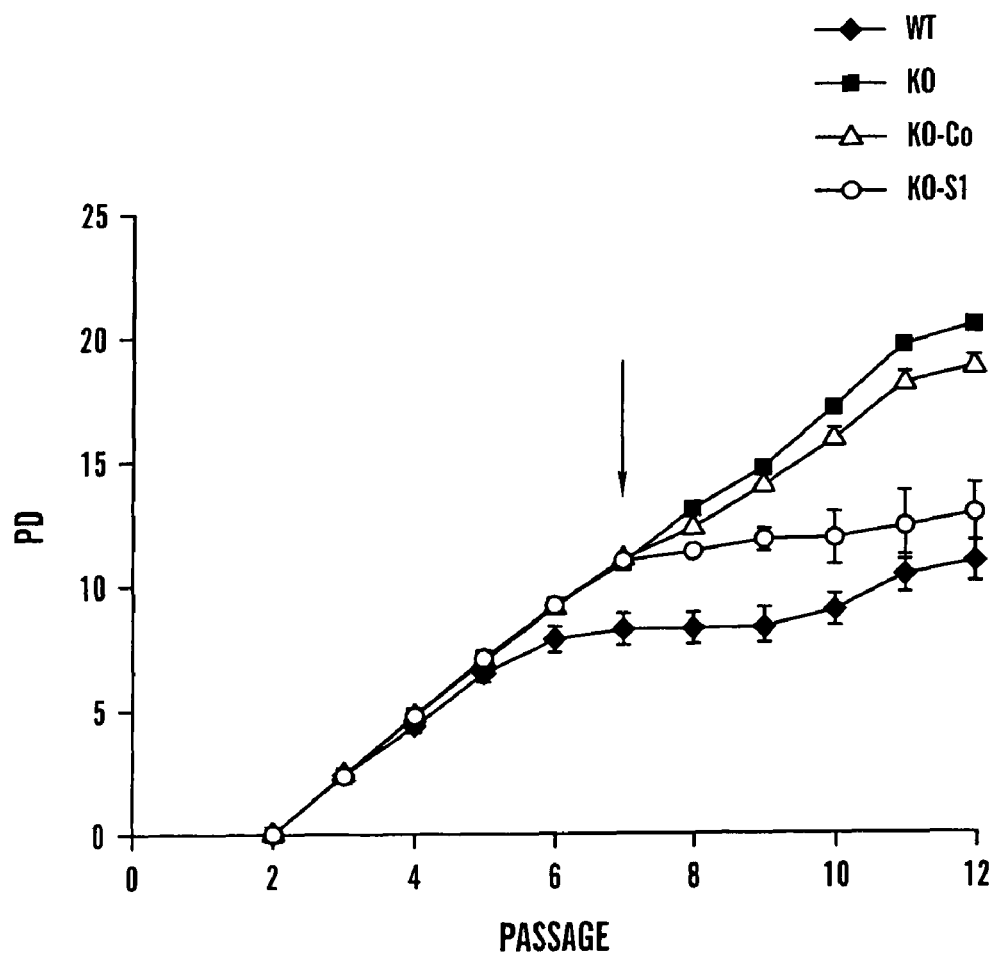
Figure 2A:
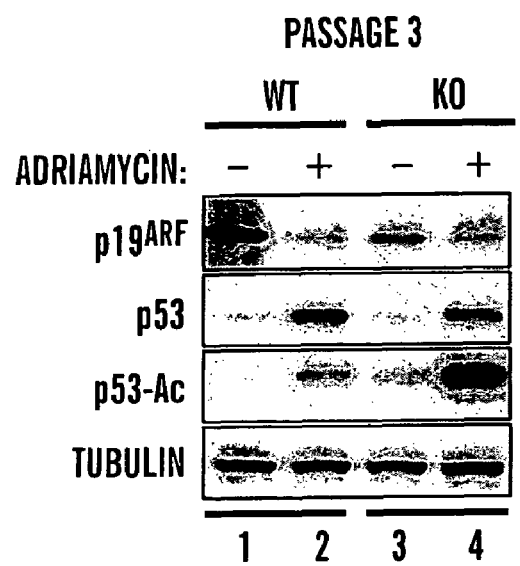
FIGS. 2A-2D show Western analysis.
Figure 2B:
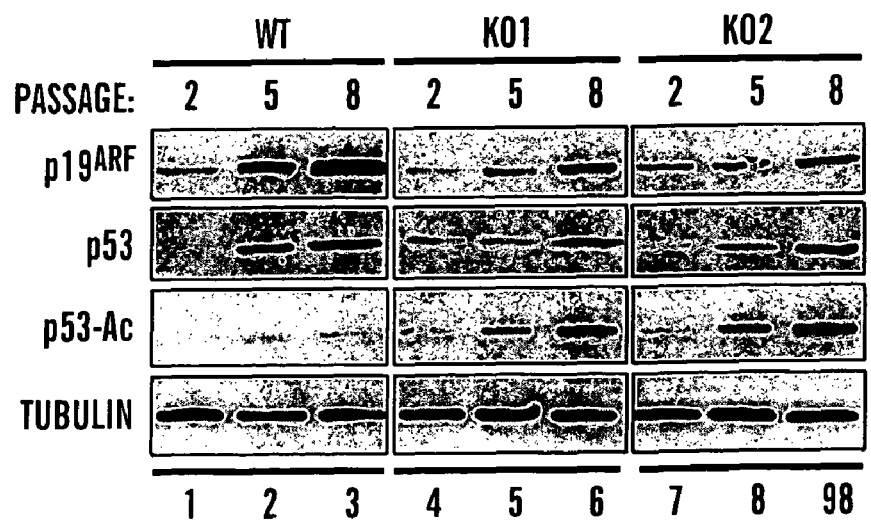
Figure 2C:
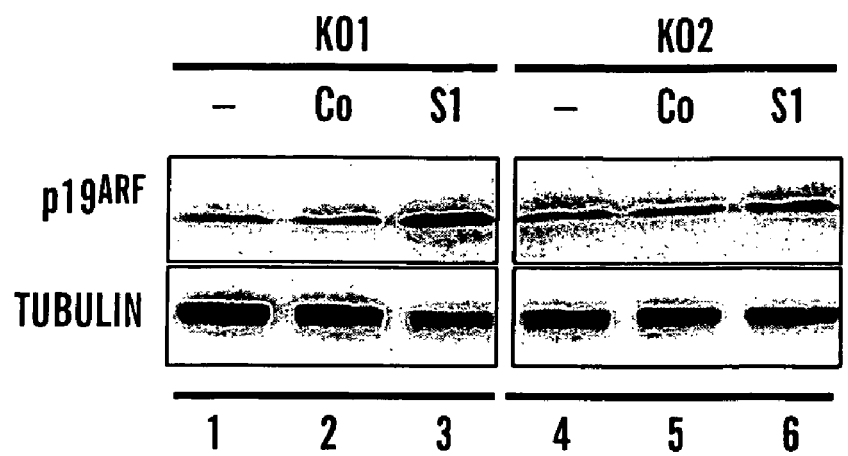
Figure 6A:
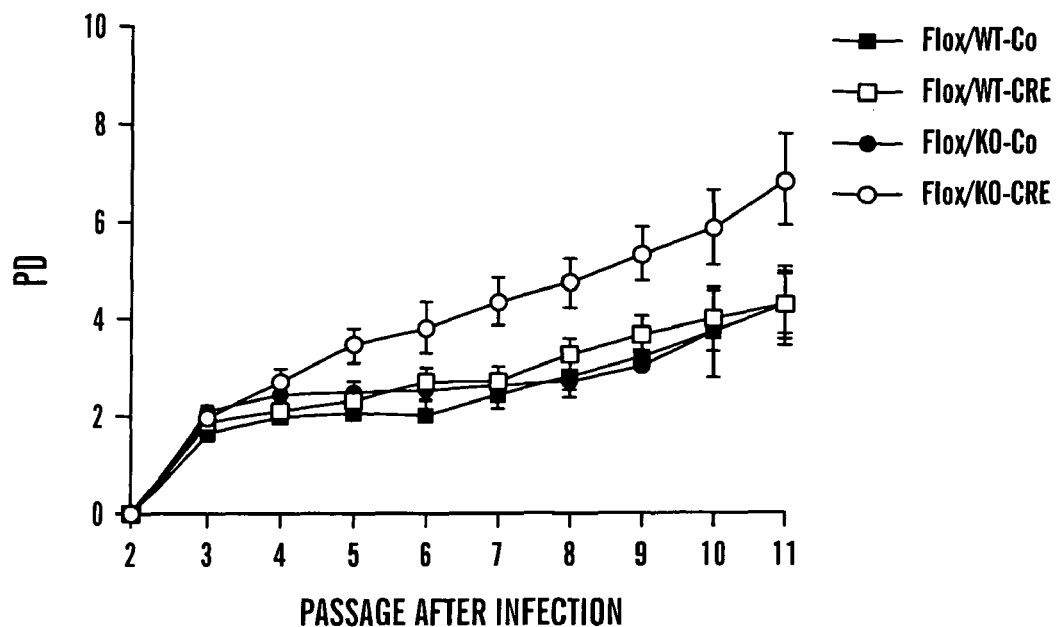
FIGS. 6A-6F show SIRT1-deficiency extends replicative lifespan.
Figure 6B:
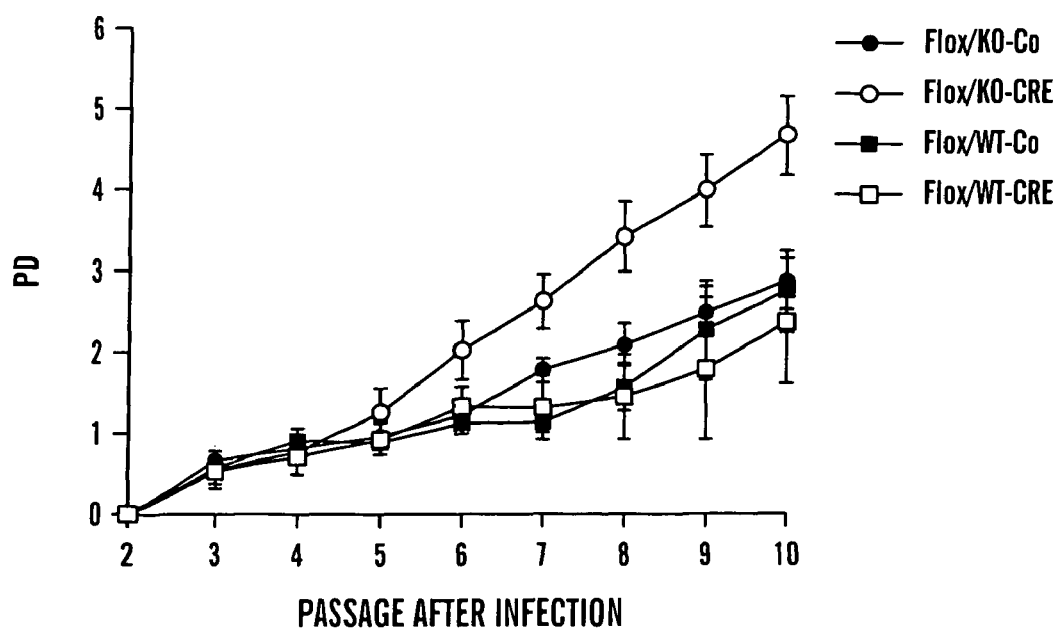
Figure 6C:
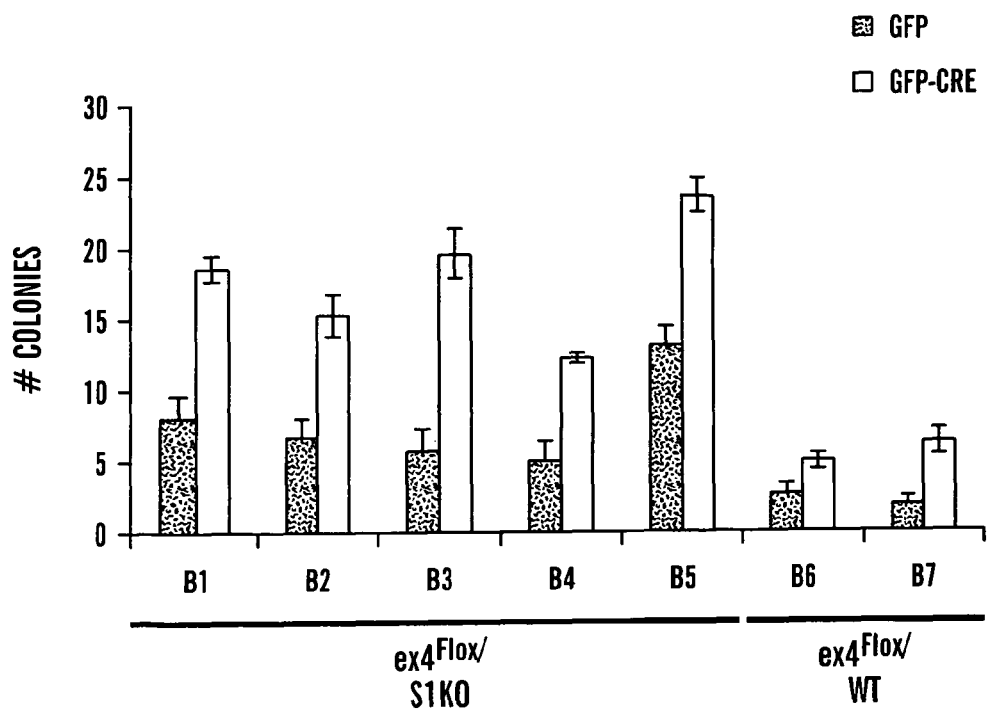
Figure 6D:
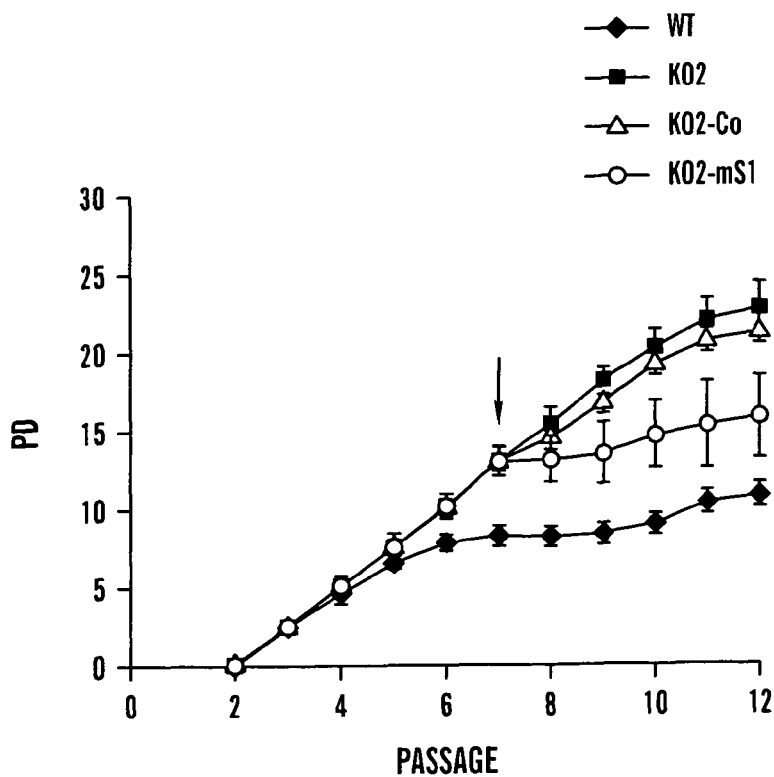
Figure 6E:
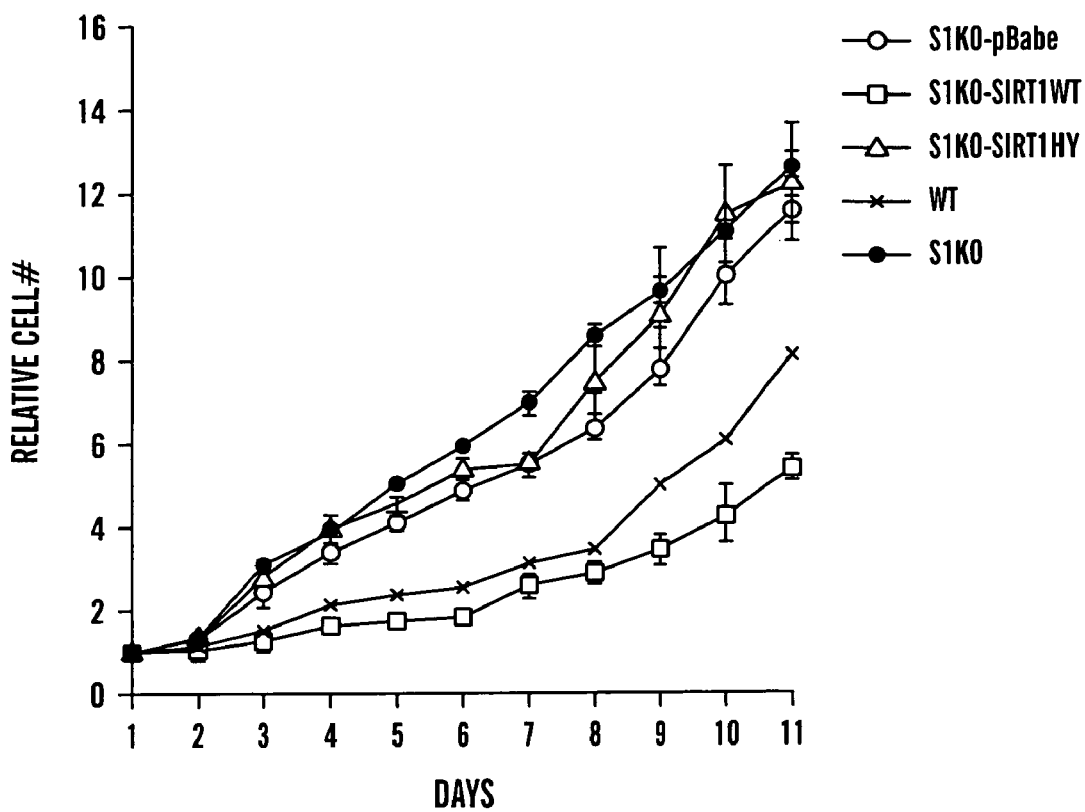
Figure 6F:
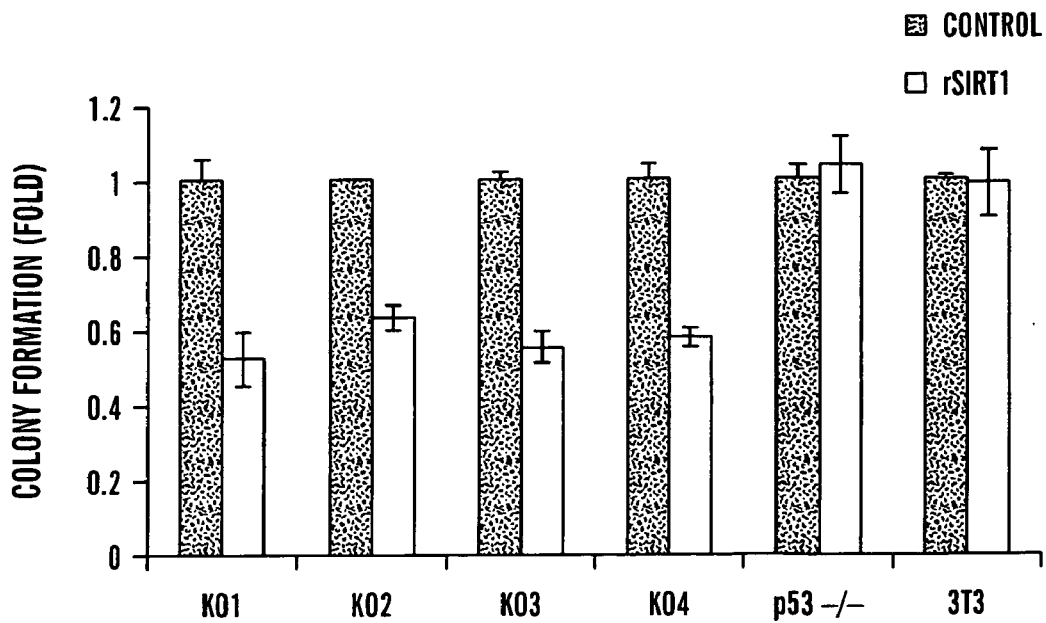
Figure 7A:
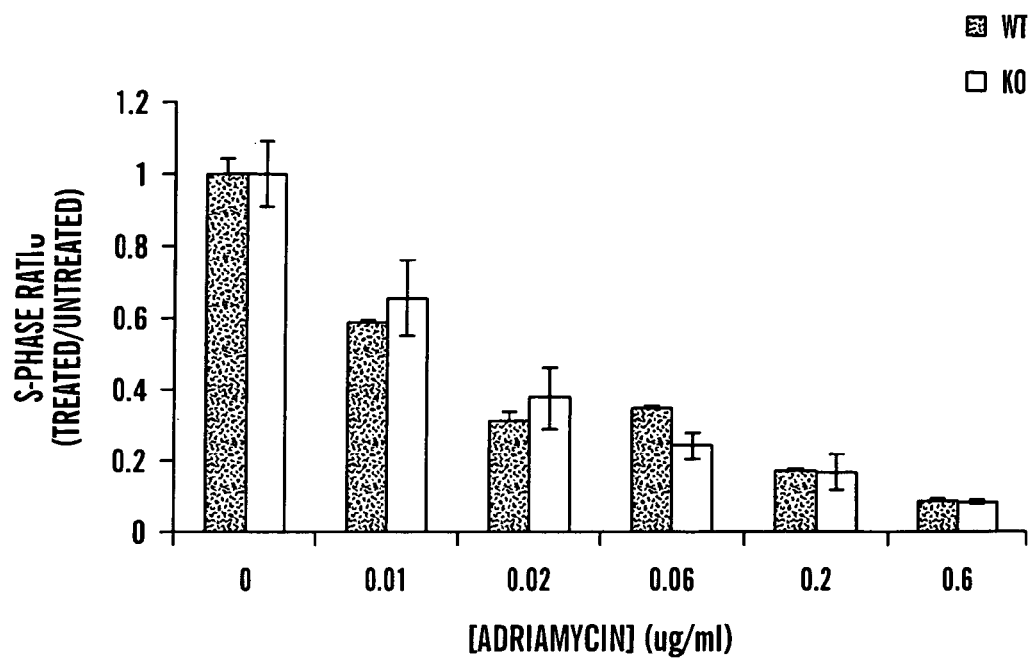
FIGS. 7A-7B show cell-cycle arrest in response to the indicated doses of adriamycin (FIG. 7A) and ionizing radiation (FIG. 7B). For both adriamycin and ionizing radiation experiments, cells were subjected to a four hour BrdU pulse 18 hours following treatment, and BrdU incorporation determined by flow cytometry. Data represent the mean of three independent cell lines and error bars indicate the standard error of the mean.
Figure 7B:
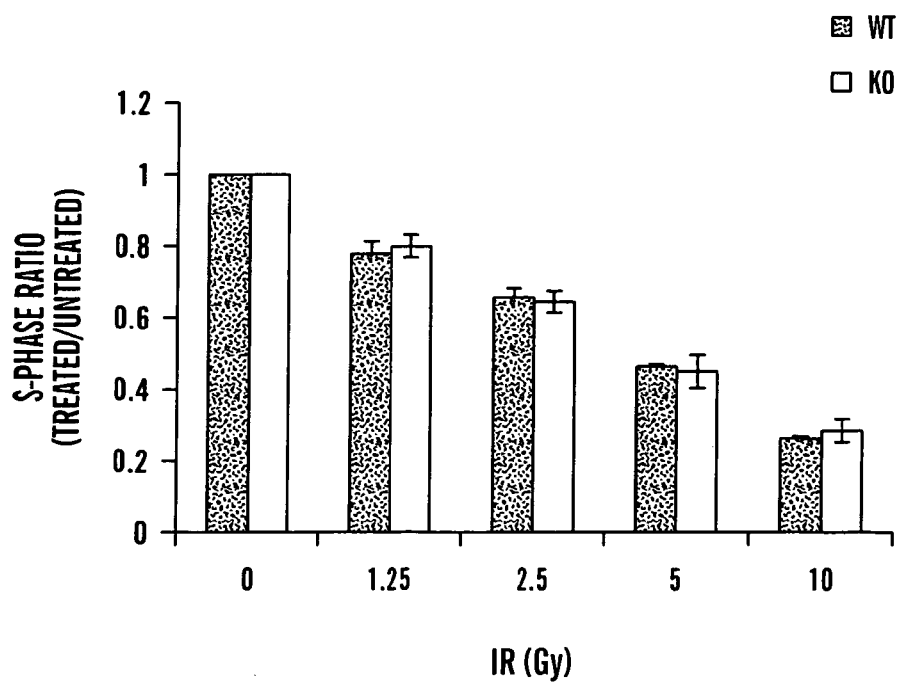

To further exclude potential secondary mutations as causes of the enhanced replicative lifespan of S1KO MEFs, we asked whether the effect of SIRT1-deficiency on replicative lifespan could be reversed by exogenous SIRT1 expression. Recombinant SIRT1 was introduced into S1KO MEFs by retroviral transduction at passage 7, a point by which WT cultures had already senesced. Transduced SIRT1 expression occurred at levels slightly lower than those of endogenous SIRT1 (FIG. 1E). Upon SIRT1 reconstitution, the S1KO MEF cultures showed significantly reduced proliferative capacity compared to control cultures treated with empty virus (FIG. 1F, and data not shown). Similar results were obtained with multiple independent late-passage S1KO MEF cultures in either serial passage or colony formation assays (FIG. 6). Notably, the deacetylase activity of SIRT1 is required for reversal of the enhanced proliferation of S1KO MEFs, since a catalytically inactive SIRT1 mutant protein failed to rescue the S1KO phenotype (FIG. 6E). Overall, these findings provide strong evidence that the resistance of S1KO MEFs to replicative senescence is a direct consequence of SIRT1-deficiency, and not due to secondary immortalizing mutations. This conclusion is further supported by our finding that SIRT1 reconstitution also led to up-regulation of a downstream regulator of replicative senescence (see below).

p19$^{ARF}$ is a Novel Downstream Effector of SIRT1 in Regulation of Replicative Senescence We previously showed that S1KO MEFs exhibited normal sensitivity to ionizing radiation, adriamycin, and to UV (Cheng et al., 2003) (FIG. 7). Thus, even though S1KO MEFs are resistant to replicative senescence, they retain normal cell-cycle control in response to various forms of DNA damage. Because p19$^{ARF}$ is a critical senescence regulator, but does not function in acute DNA damage responses (Kamijo et al., 1997; Stott et al., 1998), we asked whether SIRT1 regulates p19$^{ARF}$ levels. Western analysis of p19$^{ARF}$ levels in early passage (P3) S1KO and WT MEFs revealed that base-line levels of the p19$^{ARF}$ protein were significantly lower in S1KO cells compared to WT cells (FIG. 2A, lanes 1 and 3). In contrast, there was no difference in p19$^{ARF}$ levels in WT and S1KO cells following treatment with the DNA damage-inducing agent adriamycin (FIG. 2A, lanes 2 and 4). Over the course of serial passage, p19$^{ARF}$ accumulates in WT MEFs as previously described (Zindy et al., 1998); however, in S1KO MEFs, p19$^{ARF}$ accumulation was significantly attenuated (FIG. 2B). The p19$^{ARF}$ protein regulates senescence, at least in part, by stabilizing p53 (Kurokawa et al., 1999; Pomerantz et al., 1998). Consistent with this function of p19$^{ARF}$, S1KO cells also showed attenuated accumulation of p53 over serial passage (FIG. 2B). On the other hand, p53 was hyperacetylated in S1KO cells both following DNA damage (FIG. 2A; (Cheng et al., 2003) and also during serial passage (FIG. 2B). Thus, SIRT1-deficiency has two distinct effects on p53: hyperacetylation and reduction in total levels.

Because silencing of p19$^{ARF}$ expression is commonly observed during the spontaneous immortalization of WT MEFs that occurs upon extended passage in culture (Kamijo et al., 1997), reduced p19$^{ARF}$ levels in S1KO MEFs theoretically might reflect such a random event rather than a direct functional consequence of absence of SIRT1 expression. To address this issue, we asked whether reconstitution of late passage S1KO cells with SIRT1 expression could reverse the reduced p19$^{ARF}$ levels, in addition to reversing their enhanced replicative potential (see FIG. 1F). In three independent experiments, reconstitution of S1KO MEFs at passage 7 resulted in increased levels of p19$^{ARF}$ (FIG. 2C) and p53 (data not shown). Therefore, we conclude that the reduced p19$^{ARF}$ levels in S1KO MEFs results from loss of a novel SIRT1 function, rather than from secondary adaptive mutations or silencing events.

Figure 2D:
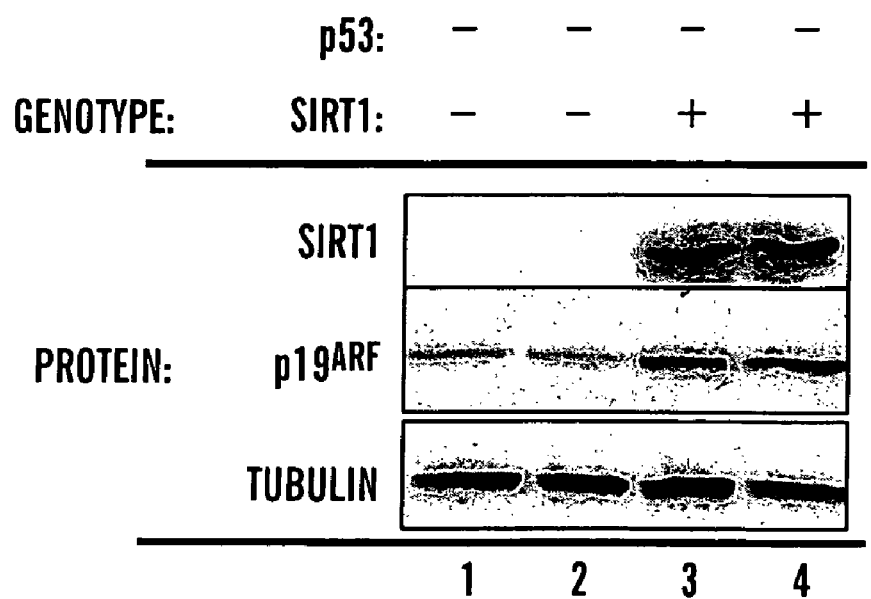

Although p19$^{ARF}$ regulates p53 stability, p53 also appears to regulate p19$^{ARF}$ in a negative feedback loop (Quelle et al., 1995). Because SIRT1-deficiency leads to p53 hyperacetylation, the resulting potential increase in p53 activity might, in theory, lead to selection for cells that have down-regulated p19$^{ARF}$. To explore this possibility, we bred mice with homozygous inactivating mutations in both SIRT1 and p53 and then generated S1KO/p53-deficient MEFs. Assays of the doubly-deficient MEFs demonstrated that, even in a p53-deficient background, SIRT1-deficiency led to reduced p9$^{ARF}$ protein levels (FIG. 2D). Thus, the reduced levels of p19$^{ARF}$ in S1KO cells cannot be attributed to feedback from p53 hyperacetylation or an adaptation to putative p53 hyperactivity. Together, our observations suggest that SIRT1 has a novel function in regulating replicative senescence by promoting up-regulation of p19$^{ARF}$.

Figure 3A:
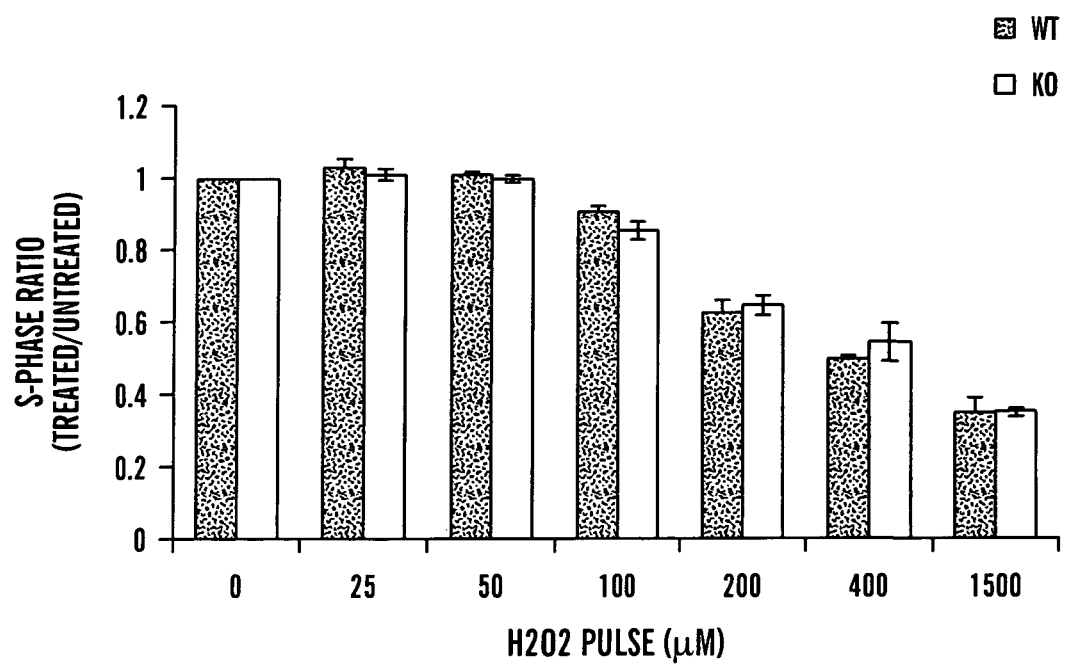
FIGS. 3A-3E show SIRT1 regulates proliferative capacity under chronic, mild oxidative stress.

SIRT1-Deficient Cells Show Enhanced Proliferative Capacity under Conditions of Chronic, Sub-Lethal Oxidative Stress Because replicative senescence in MEFs is thought to be a response to the non-physiologic levels of oxidative stress present in standard cell culture conditions (Parrinello et al., 2003), we asked whether and in what context SIRT1 regulates oxidative stress resistance. S1KO and WT cultures were treated with a wide range of doses of $H_2O_2$ for 15 minutes, transferred to normal media for 18 hours, and the percentage of S-phase cells assessed by BrdU incorporation to determine the ratio of BrdU incorporation in $H_2O_2$-treated cells compared to control treated cells (S-phase ratio). At all doses assayed, the S-phase ratios of S1KO cells and WT control cells were indistinguishable (FIG. 3A). These data indicated that, under the conditions of this assay, SIRT1-deficiency does not confer resistance to acute oxidative stress. This observation was somewhat unexpected, given that replicative senescence is in fact a response to oxidative stress. However, since replicative senescence reflects a cellular response to continuous culture under mild chronic oxidative stress, it is conceivable that such conditions might trigger different cellular responses than acute oxidative insults.

Figure 3B:
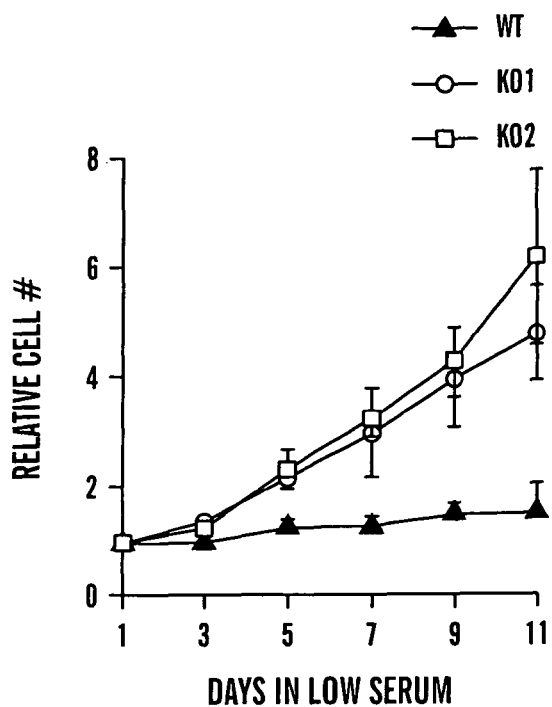
Figure 3B:
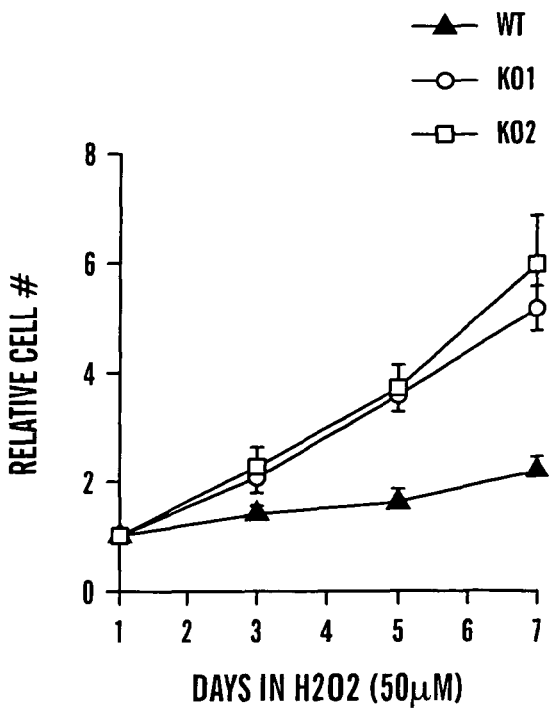
Figure 3C:
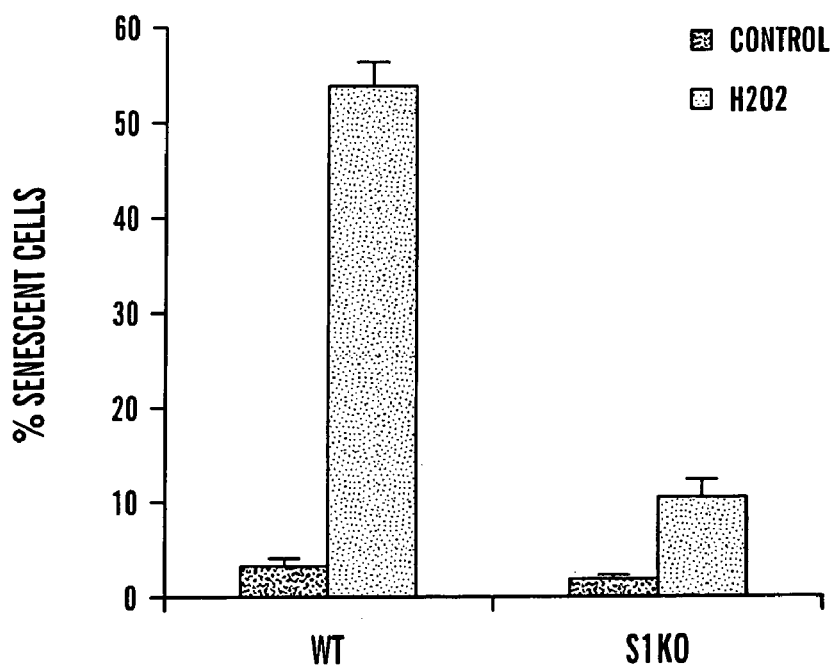
Figure 3D:
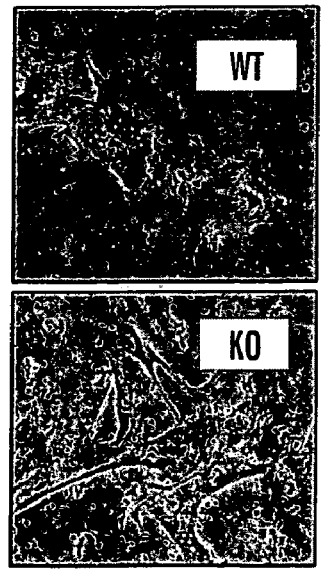
Figure 3E:
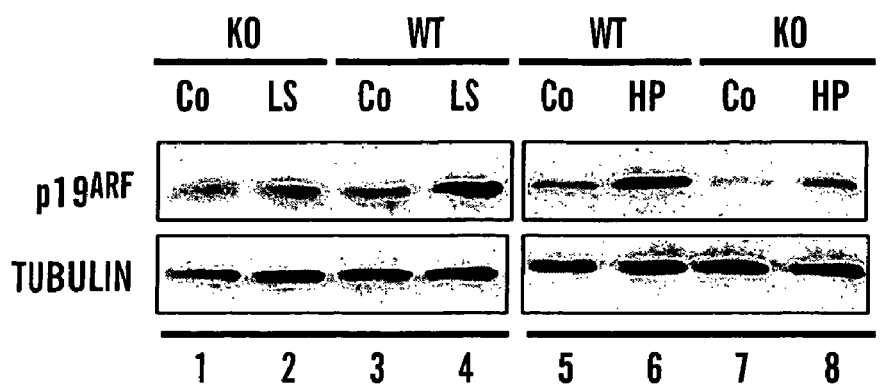
Figure 8A:
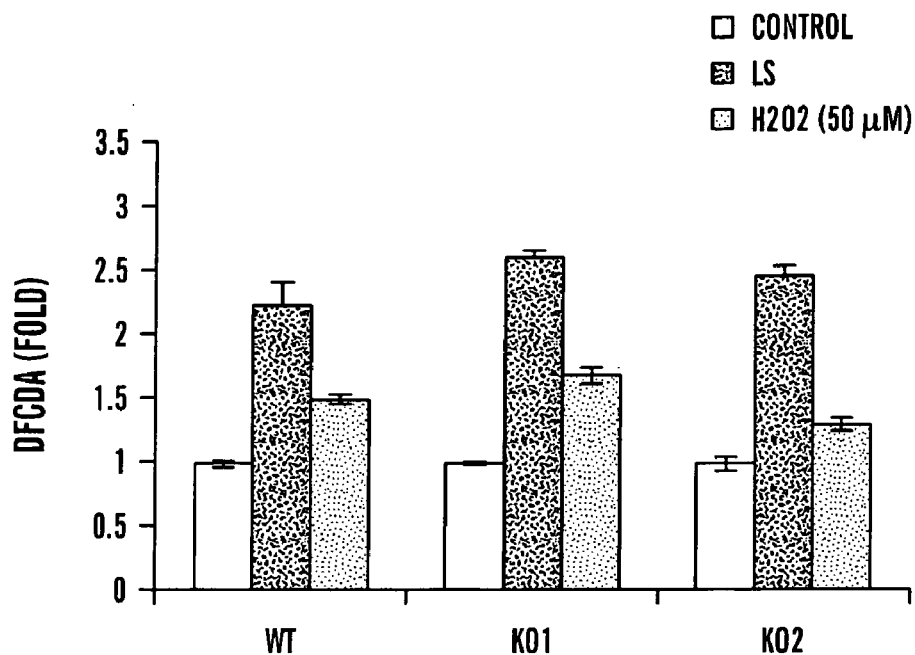
FIGS. 8A-8C show oxidative stress measurements following culture in chronic sub-lethal oxidative conditions, and exposure to oncogenic Ras.

To test whether S1KO MEFs have enhanced replicative potential under conditions of chronic, sub-lethal oxidative stress, we tested them for growth in the continuous presence of 50 uM $H_2O_2$ or under serum deprivation, conditions which led to mild oxidative stress and accelerated cell-cycle arrest/senescence of WT MEFs (Nemoto and Finkel, 2002); (FIG. 8A). Under both these conditions, S1KO MEFs proliferated significantly better than WT MEFs (FIG. 3B), and accumulated lower levels of p19$^{ARF}$ (FIG. 3E). Further, at the end of 1 week of culture under these conditions, greater than 50% of WT MEFs stained positive for the senescence marker SA-β-galactosidase; whereas only about 10% of S1KO MEFs were SA-β-galactosidase positive (FIG. 3C). In these experiments, S1KO or WT MEFs did not undergo apoptosis as assessed by annexin V staining (data not shown). Together, these observations indicate that the resistance of S1KO MEFs to replicative senescence reflects a novel function of SIRT1 in controlling proliferative capacity under conditions of chronic, sub-lethal oxidative stress.

SIRT1-Deficient Cells Retain Intact Responses to Oncogenic Ras

Figure 4A:
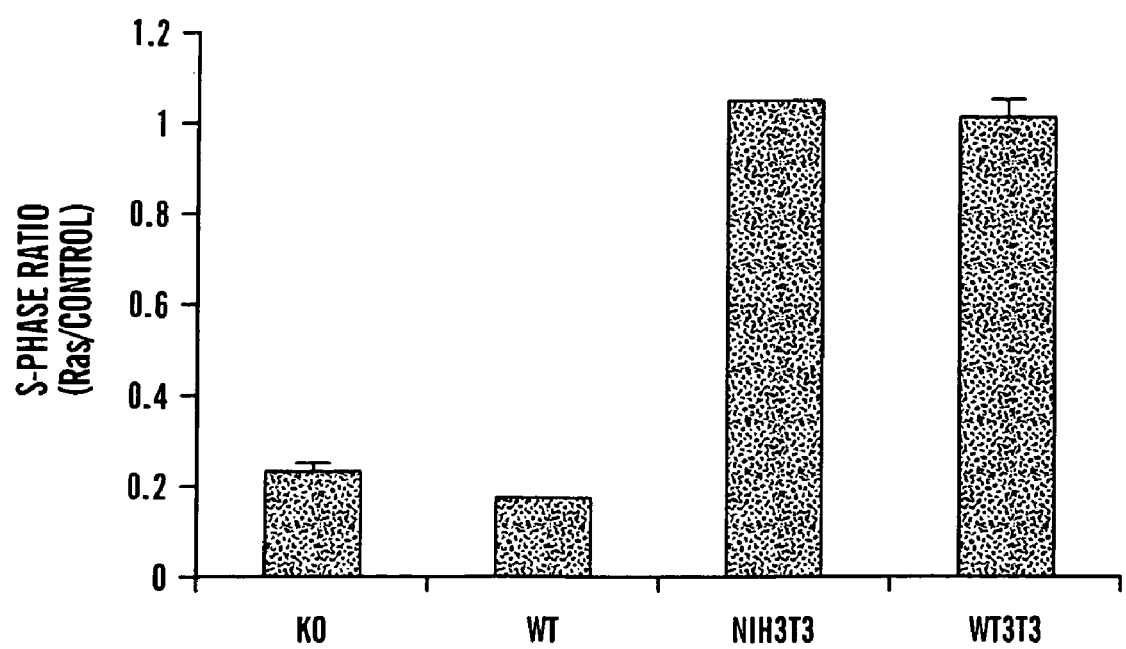
FIGS. 4A-4C show SIRT1 is dispensable for oncogene-induced premature senescence.
Figure 4B:
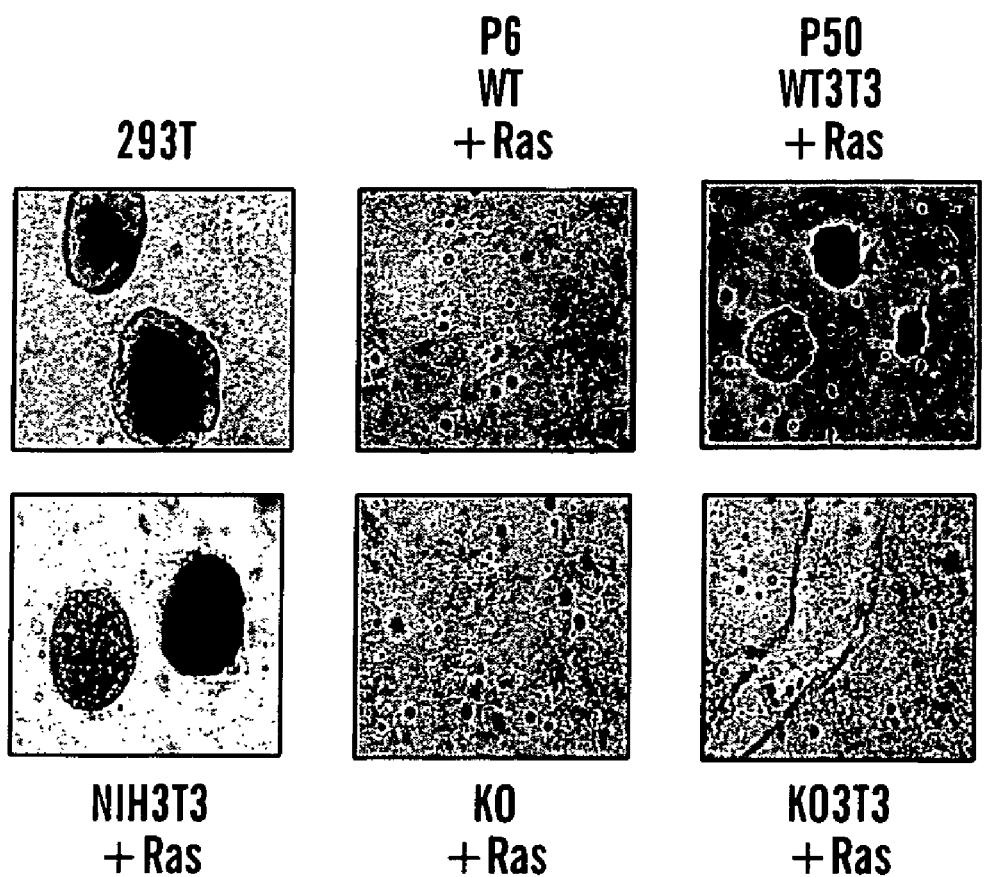
Figure 4C:
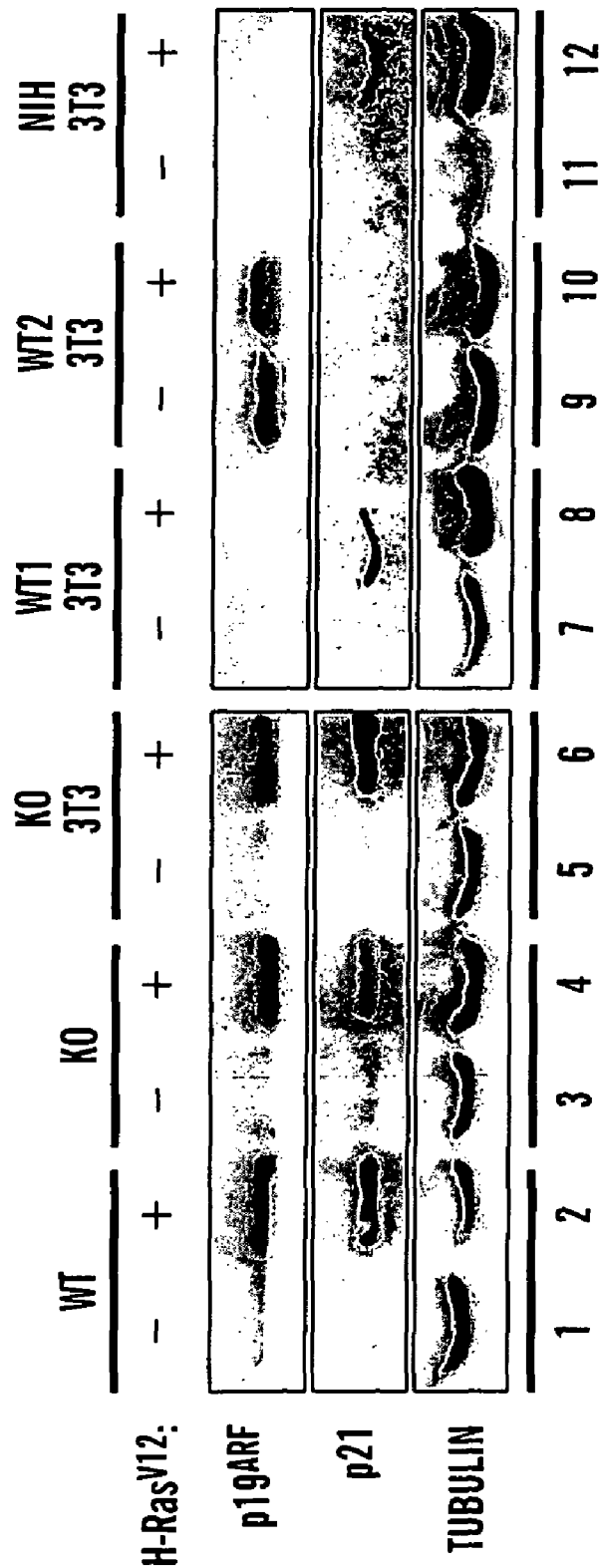

We next asked whether SIRT1 regulates p19$^{ARF}$ levels and premature senescence of MEFs in response to oncogenic Ras. The activated Ras mutant H-Ras$^{V12}$ (or empty virus control) was introduced into S1KO and WT MEFs by retroviral transduction, and cell-cycle arrest assessed by BrdU incorporation. Unlike immortal 3T3 MEF lines (Kamijo et al., 1997), S1KO MEFs showed entirely normal responses to H-Ras$^{V12}$ with respect to cell-cycle arrest (FIG. 4A). We also carried out soft agar assays for anchorage-independent growth, a characteristic of cellular transformation. When transduced with H-Ras$^{V12}$, S1KO MEFs failed to form colonies in soft agar, like primary WT MEFs; whereas H-Ras$^{V12}$-expressing immortal 3T3 lines exhibited robust anchorage-independent colony formation (FIG. 4B). Moreover, there was no significant difference in levels of p19$^{ARF}$ induction in S1KO and WT MEFs (FIG. 4C), indicating that SIRT1 is dispensable for p19$^{ARF}$ induction in response to H-Ras$^{V12}$-expression. Similar results were obtained for three independent S1KO MEF lines. Thus, SIRT1 is required for normal p19$^{ARF}$ induction and cellular senescence in response to prolonged replication but is dispensable for senescence in MEFs following acute expression of oncogenic Ras.

Figure 9A:
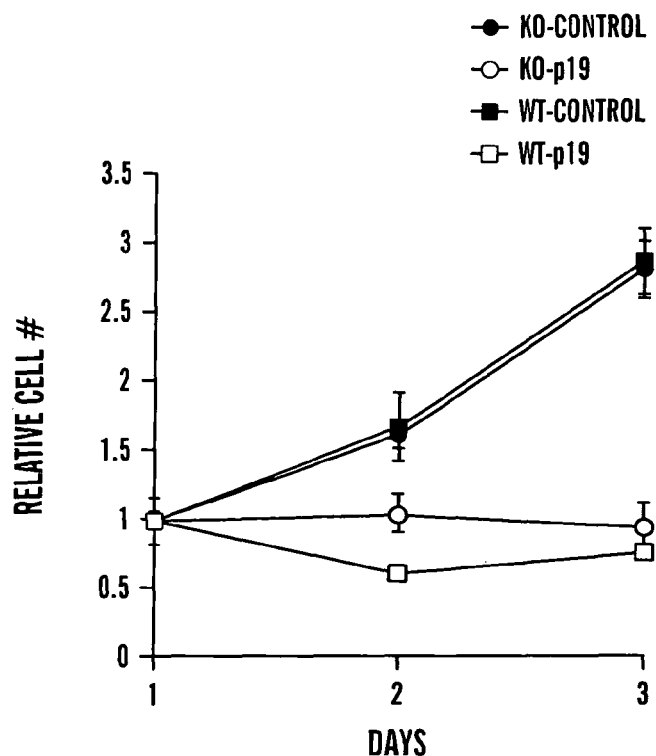
FIGS. 9A-9D show SIRT1-deficient MEFs retain intact responses to p19$^{ARF}$, p16$^{INK4A}$, and c-myc.
Figure 9B:
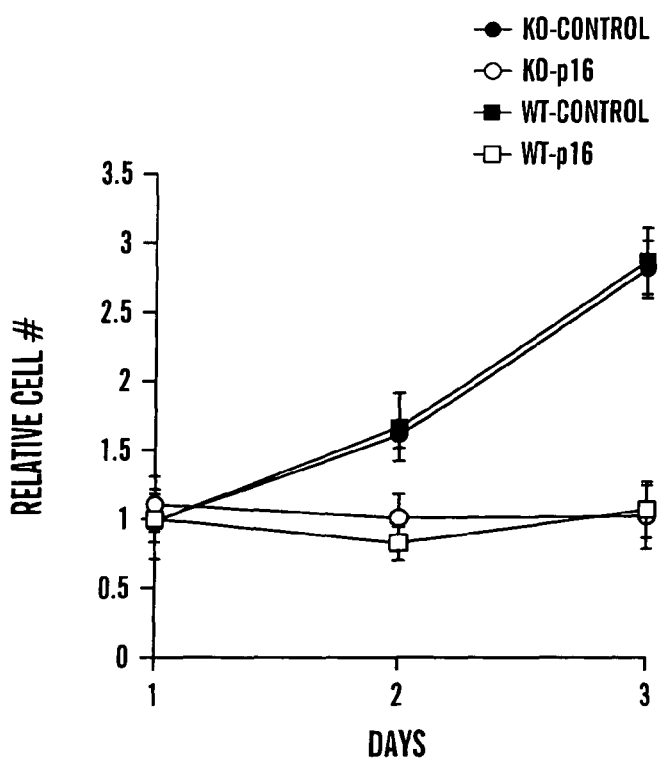
Figures 9C, 9D:
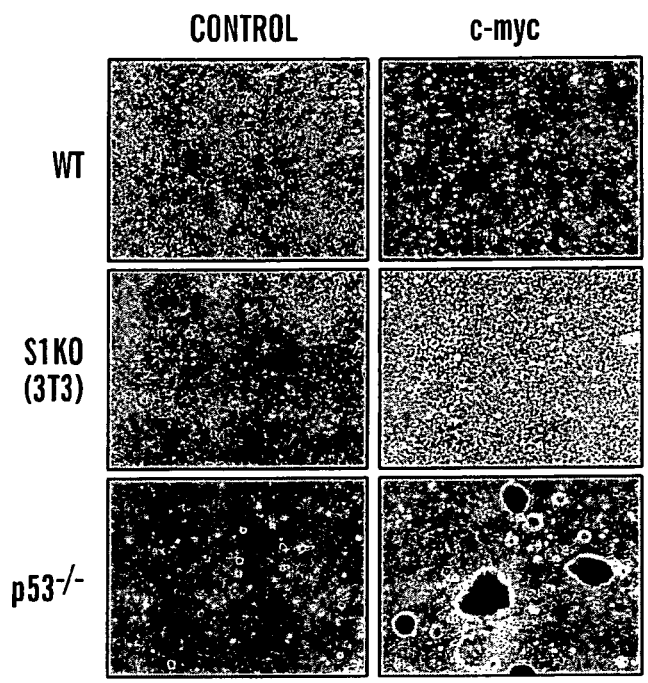

Notably, S1KO cells were sensitive to H-Ras$^{V12}$-induced senescence and resistant to H-Ras$^{V12}$-induced transformation, even at very late passages (passage 50) (FIG. 4B). This is in sharp contrast to the cells that grow out of WT MEF cultures following such extended passage, which are transformed by activated H-Ras$^{V12}$ (FIG. 4B). In this context, cells that have grown out of WT MEF cultures by passage 50 had, as expected (Kamijo et al., 1997), either lost p53-dependent induction of the cell-cycle regulator p21 (FIG. 4C, WT2-3T3) or expression of p19$^{ARF}$ (FIG. 4C, WT1-3T3) in response to H-Ras$^{V12}$. In contrast, S1KO cultures at passage 50 (FIG. 4C, KO-3T3) showed normal p19$^{ARF}$ and p21 induction in response to H-Ras$^{V12}$. S1KO MEFs also arrested normally in response to acute expression of p19$^{ARF}$ (FIGS. 9A and B), indicating that the pathway downstream of p19$^{ARF}$ is functionally intact. We also found that the p16$^{INK4A}$/pRb pathway was intact in SIRT1KO MEFs (FIG. 9B). In addition, S1KO MEFs also were not transformed by oncogenic c-myc, in contrast to immortal MEF lines carrying adaptive mutations (FIGS. 9C and D). We conclude that SIRT1-deficiency allows for continued proliferation of MEFs without subjecting them to selection for immortalizing mutations.

SIRT1 Regulation of Cellular Lifespan via p19$^{ARF}$

Figure 5:
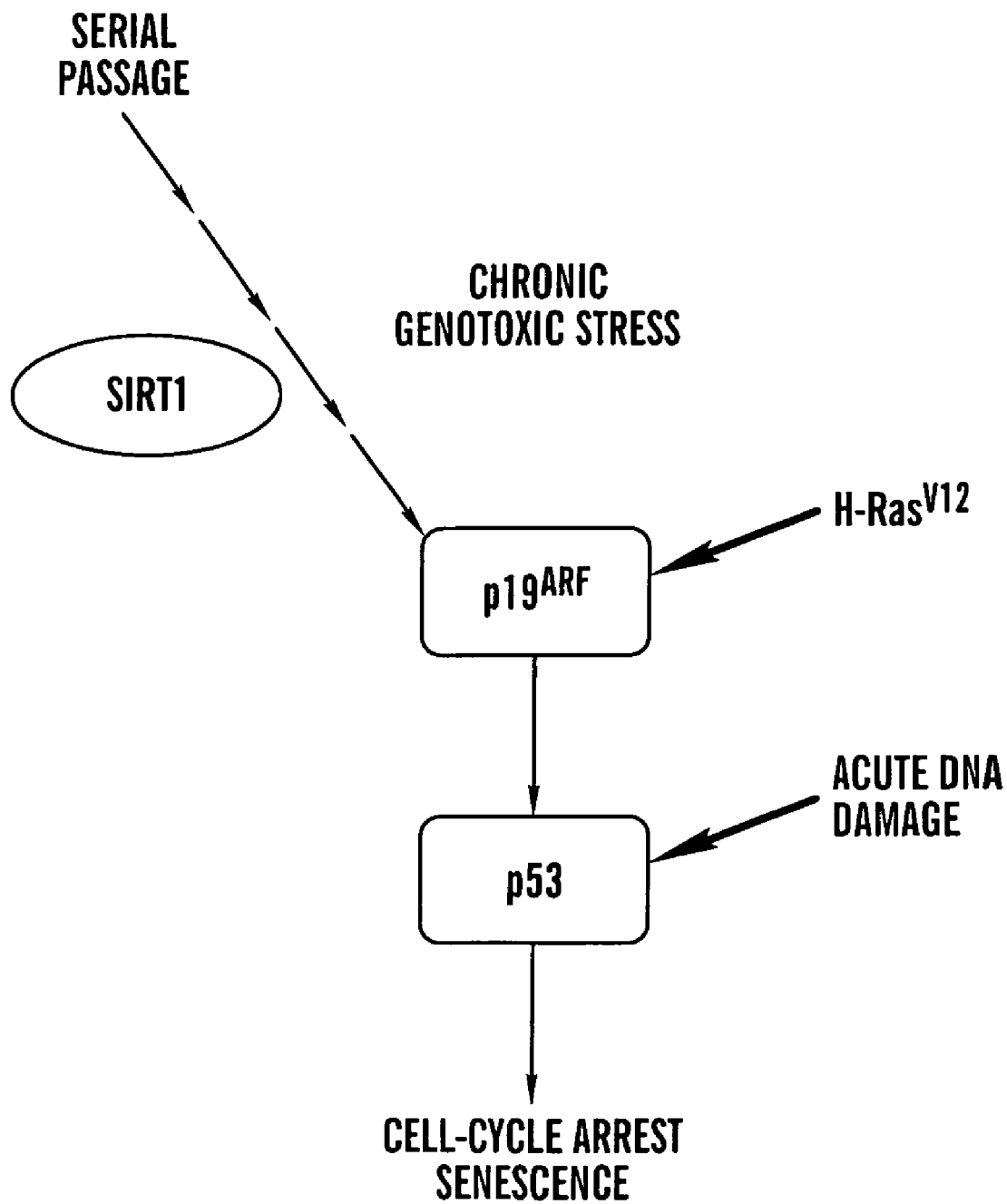
FIG. 5 shows that SIRT1 promotes senescence in response to prolonged replication, but not oncogene activation or acute DNA damage. Acute DNA damage insults activate p53 by $p19^{ARF}$-independent mechanisms, whereas replicative senescence, which is due to chronic, sub-lethal oxidative stress, and Ras-induced premature senescence activate p53 by inducing $p19^{ARF}$. These findings suggest that SIRT1 is required for $p19^{ARF}$ induction only during replicative senescence, in response to chronic, sub-lethal genotoxic stress.

Our findings lead to the surprising conclusion that mammalian SIRT1 and budding yeast Sir2 have opposite effects on replicative senescence. Thus, while Sir2 extends replicative lifespan in budding yeast, SIRT1 functions to limit the replicative lifespan of MEFs. We also note that, similar to our results with MEFs, RNAi-mediated knock-down of SIRT1 dramatically extends replicative lifespan of human primary fibroblasts (E. Michishita, I. Horikawa, and J. C. Barret, personal communication), documenting the generality of this function across mammalian species. We also show that alleviation of replicative senescence in the absence of SIRT1 correlates with up-regulation of p19$^{ARF}$. Because p19$^{ARF}$ promotes stabilization of p53, SIRT1-deficiency in MEFs also impairs normal up-regulation of p53 levels during prolonged culture, which likely accounts for bypass of senescence. However, in contrast to many mutations that confer resistance to replicative senescence, SIRT1-deficiency in MEFs leaves intact cell-cycle arrest/senescence responses to acute DNA damage, acute oxidative stress, and activated oncogenes. Overall, our findings also support the notion that mammalian cells have evolved different mechanisms to respond to chronic versus acute genotoxic insults (FIG. 5).

Figure 10A:
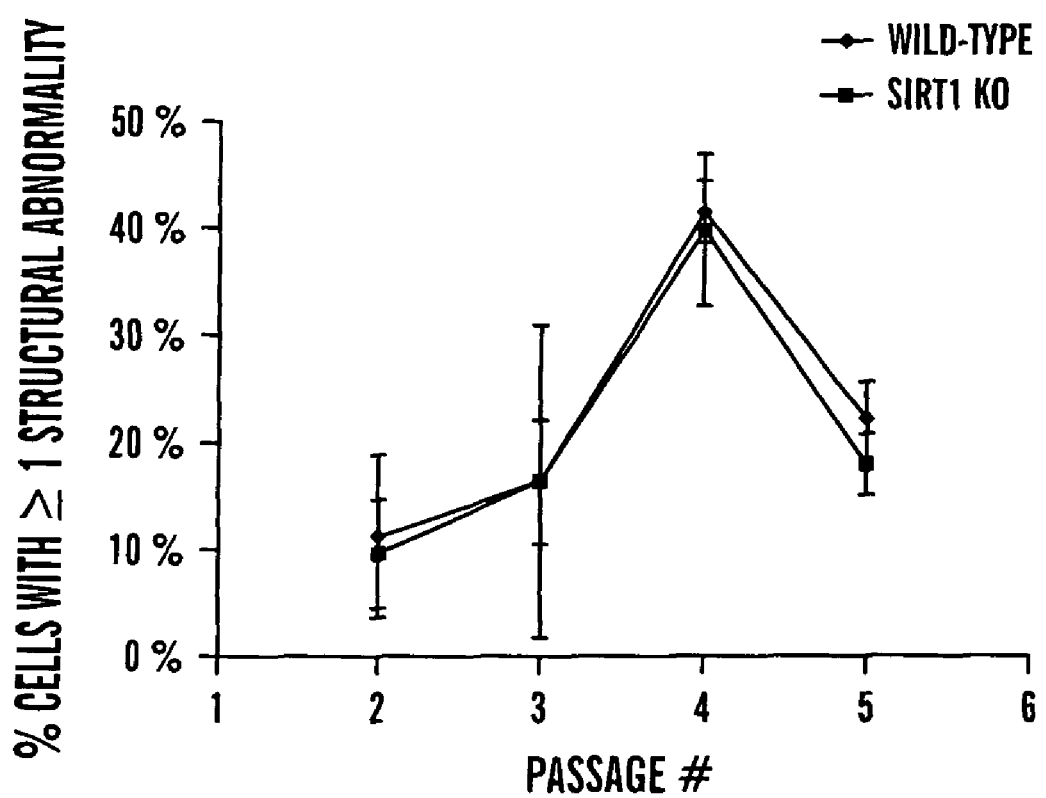
Figure 10B:
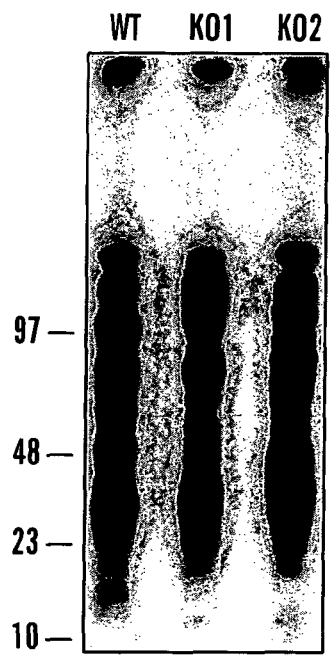
Figure 10C:
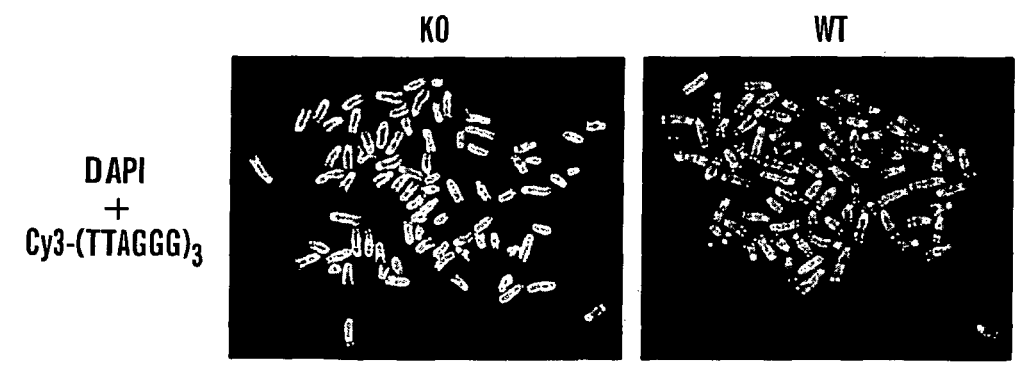

Several lines of evidence indicate that the effects of SIRT1-deficiency on p19$^{ARF}$ and replicative senescence are not due to adaptive changes in S1KO cultures. First, acute inactivation of SIRT1 by Cre-Lox strategies confers resistance to senescence. Second, the enhanced replicative potential and attenuated p19$^{ARF}$ levels of S1KO cells can be reversed by exogenous SIRT1, even at relatively late passage, when wild-type cultures have already senesced. Third, SIRT1-deficiency leads to reduced p19$^{ARF}$ levels in a p53-deficient background, in which there should be no selection pressure for cells expressing low levels of p19$^{ARF}$. Fourth, unlike immortalized cell lines that have acquired secondary adaptations in culture, SIRT1-deficient MEFs retain fully functional responses to activated oncogenes and acute DNA damage that are indistinguishable from those of primary wild-type MEFs. We have also found that although SIRT1-deficient MEFs bypass senescence, they do not accumulate genomic instability beyond that observed in wild-type cells (FIG. 10). These results are consistent with data found in p19$^{ARF}$ deficient MEFs, where cellular immortalization is not accompanied by increased genomic instability (Kamijo et al., 1997; Zindy et al., 1997). Thus, the similarity of the phenotypes resulting from p19$^{ARF}$- and SIRT1-deficiency with respect to extending MEF lifespan in the absence of increased genomic instability further supports our conclusion that the effect of SIRT1-deficiency on MEF replicative lifespan ultimately is mediated through p19$^{ARF}$. Together, these findings argue that the resistance of S1KO cells to replicative senescence reflects a novel function of SIRT1 that influences regulation of p19$^{ARF}$ expression in response to chronic genotoxic stress.

Figure 8B:
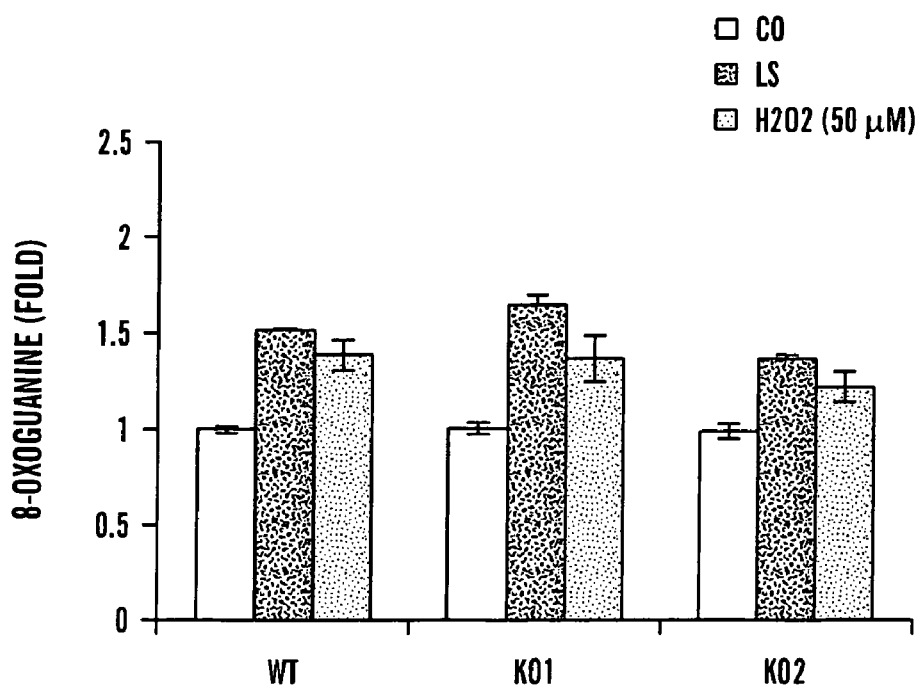
Figure 8C:
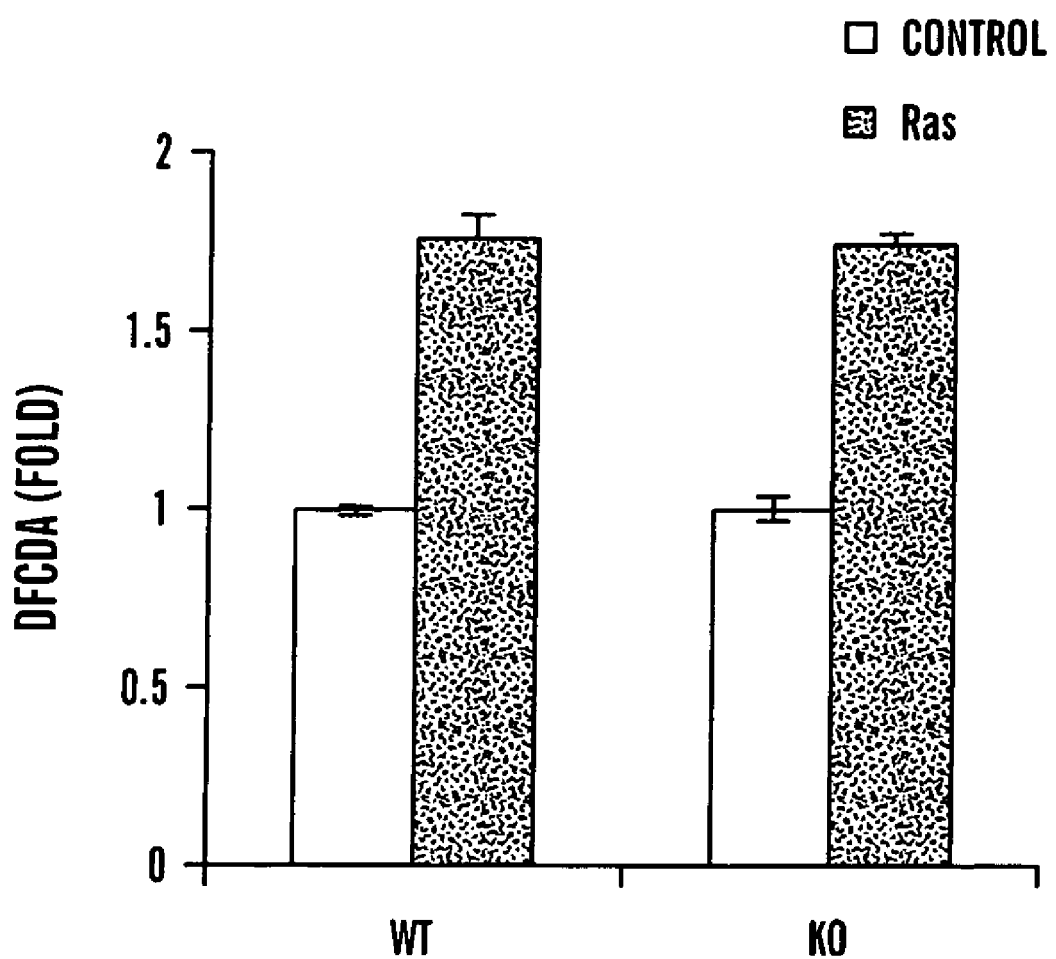

Differential Regulation of p19$^{ARF}$ by SIRT1 Distinguishes Replicative from Oncogene-Induced Senescence The p19$^{ARF}$ protein is a critical regulator of cellular senescence; correspondingly, it is up-regulated during both replicative senescence and oncogene-induced premature senescence (Palmero and Serrano, 2001; Zindy et al., 1998). It has been proposed that replicative senescence and oncogene-induced senescence may not be functionally distinct (Ben-Porath and Weinberg, 2004). In this context, both processes are thought to result from increased cellular levels of reactive oxygen species (ROS) (Irani et al., 1997; Lee et al., 1999; Parrinello et al., 2003; Sundaresan et al., 1996). However, we now show that SIRT1 is required for normal up-regulation of p19$^{ARF}$ during replicative senescence in response to chronic, sub-lethal genotoxic stress; but it is not required for activated Ras-induced premature senescence. One conceivable mechanism by which these two processes might differ would be by triggering different levels of ROS. However, our preliminary data suggests we found that both forms of stress induction in MEFs led to similar intracellular levels of ROS (FIG. 8). Thus, the differential involvement of SIRT1 in replicative versus oncogene-induced senescence points to a fundamental distinction in the pathways underlying these phenomena, even though both are ultimately mediated by p19$^{ARF}$ (See model, FIG. 5). In this regard, while genotoxic stress is the primary trigger for replicative senescence, increased ROS levels is only one of several consequences of mitogenic signaling evoked by activated Ras (Irani et al., 1997).

We can tentatively rule out several potential mechanisms by which SIRT1 might regulate p19$^{ARF}$ in the context of replicative senescence. In particular, SIRT1 does not function directly to deacetylate p19$^{ARF}$ based on assays with available anti-acetyl lysine antibodies (data not shown). Also, direct regulation of histones at the p19$^{ARF}$ promoter by SIRT1 seems unlikely to account for reduced p19$^{ARF}$ levels in S1KO cells; since histone hyperacetylation should increase, rather than decrease, p19$^{ARF}$ expression. Thus, SIRT1 may target, directly or indirectly, an upstream p19$^{ARF}$ regulator. Such a putative SIRT1 substrate could be part of the senescence response to chronic genotoxic stress, or alternatively, could regulate the of induction the senescence response itself. In the latter context, the lack of p19$^{ARF}$ accumulation in S1KO cells could simply reflect the failure of these cells to accumulate a threshold level of genotoxic stress required to initiate the replicative senescence response.

The regulation of p19$^{ARF}$ by SIRT1 could occur transcriptionally or post-transcriptionally. Several negative regulators of replicative senescence that regulate p19$^{ARF}$ transcription have been identified including the polycomb group proteins Bmi-1, Cited2, Twist, the transcription factors Tbx2 and Tbx3 (Carlson et al., 2002; Jacobs et al., 2000; Jacobs et al., 1999; Krane et al., 2003), and the recently identified Pokemon factor (Maeda et al., 2005). However, unlike the putative SIRT1-regulated factor, negative regulation of p19$^{ARF}$ by these factors counteracts Ras-induced premature senescence and cooperates with Ras to promote oncogenic transformation. In addition, our preliminary experiments have not revealed hyperacetylation of several of these known factors in S1KO cells. At the post-transcriptional level, there is evidence that p19$^{ARF}$ protein undergoes ubiquitin-dependent degradation (Kuo et al., 2004), and SIRT1 might deacetylate a factor involved in regulating p19$^{ARF}$ stability. However, the E2/E3 ubiquitination factors that regulate p19$^{ARF}$ turnover have yet to be identified. Thus, the identity of the putative SIRT1-target that influences replicative senescence remains unknown.

Our findings demonstrate that SIRT1 expression can influence p53 function via two distinct mechanisms, which have opposite effects on net p53 activity. Thus, SIRT1 inactivates p53 by deacetylation, but can lead to p53 induction via regulation of p19$^{ARF}$. In the context of replicative senescence in S1KO MEFs, reduced p53 levels outweigh the effects of p53 hyperacetylation. In contrast, following acute DNA damage in SIRT1-deficient thymocytes, p53 levels are unaffected, and p53 hyperacetylation renders the cells hypersensitive to DNA damage (Cheng et al., 2003). Similarly, over-expression of SIRT1 deacetylates p53 in MEFs following activated Ras expression and, thereby, appears to attenuate the senescence response (Langley et al., 2002). Therefore, as we observed no effect of SIRT1-deficiency on total p19$^{ARF}$ and p53 levels following activated Ras expression in MEFs (FIG. 4C, and data not shown), p53 hyperacetylation in these cells might be predicted to lead to a hyperactive senescence response. However, we could not assay for such a hyperactive response, because premature senescence of wild-type MEFs occurs almost immediately following transduction and selection for activated Ras-expression. Overall, our current findings, coupled with previous work, suggest that the effect of SIRT1 on net cellular p53 activity may be dependent on both cell type and the context of cellular stress.

Perspective: Cellular Senescence, Mammalian Aging and SIRT1.

Based on the ability of Sir2 to extend lifespan in lower eukaryotes, SIRT1 has been considered an attractive pharmacological target in humans. However, the divergence of yeast Sir2 and mammalian SIRT1 functions in replicative senescence highlights potential difficulties with this generalization. In this regard, the relationship between cellular senescence and organismal aging clearly differs in unicellular and multi-cellular organisms. In unicellular yeast, cellular senescence is, by definition, a detrimental process, while in mammals cellular senescence shows antagonistic pleiotropy; that is, it may be beneficial in some contexts, such as tumor suppression, but detrimental in others such as promoting aging of mitotic tissues (Campisi, 1997). Moreover, as our findings indicate that SIRT1 has different effects on senescence depending on the particular trigger, a detailed examination of its function in specific contexts would be critical in attempts to predict how modulation of SIRT1 activity would impact mammalian physiology and aging.

Regardless of the role of SIRT1 in normal physiology, our finding that "immortal" SIRT1-deficient MEFs have intact responses to acute genotoxic stress and oncogenic transformation indicates that modulation of SIRT1 activity might be useful to grow large quantities of certain cell types for experimental or therapeutic purposes without selecting for transforming mutations. Indeed, inactivation of p19$^{ARF}$ can augment expansion and long-term cultivation of mouse hepatocytes, and contribute to liver regeneration following transplantation (Mikula et al., 2004). In addition, inhibition of p19$^{ARF}$ expression can promote the self-renewal of hematopoietic stem cells, augmenting ex vivo expansion and in vivo repopulating capacity (Iwama et al., 2004). Thus, in these, and potentially other cell types, SIRT1 might be a useful target for pharmacologic modulation.

Materials and Methods

Culturing and Retroviral Reconstitution of MEFs and 3T3 Serial Passaging.

MEFs were cultured in DMEM supplemented with 15% fetal calf serum, 8 mM nonessential amino acids, 8 mM sodium pyruvate, 9 mM glutamine, 9 mM penicillin/streptomycin, 18 mM HEPES (pH7), and 0.006 mM beta-mercaptoethanol. For replicative senescence assays, a 3T3 protocol (Sherr and DePinho, 2000; Todaro and Green, 1963) was followed by counting cells in triplicate and re-seeding $3\times10^5$ cells per 10 cm plate every 3 days. For colony formation assays. MEFs were seeded at a density of $10^3$ cells per 10 cm plate, cultured for two weeks, and colonies stained with crystal violet. Retroviral packaging and infection was performed as previously described (Cheng et al., 2003). For chronic $H_2O_2$ cultures, $1\times10^6$ cells were plates in 2 ml media with 50 uM $H_2O_2$ lacking beta-mercaptoethanol in 6 well plates, and media was replaced everyday.

Generation and Cre-Deletion of Conditionally Targeted SIRT1 MEFs.

Gene-targeting to generate ex4$^{Flox}$ ES cells was previously described (Cheng et al., 2003). ES cell clones were injected into C57BL/6 blastocysts, founder chimeras bred to 129/Sv females, and F1 heterozygotes intercrossed. Resulting ex4$^{Flox}$/ex4$^{Flox}$ mice were crossed to WT/S1KO mice, and MEFs were isolated from embryonic day 13.5 embryos and genotyped by Southern analysis. For Cre deletion, conditionally targeted SIRT1 MEFs were infected with Cre-GFP and GFP adenoviruses (gift of Jonathan Walsh and Richard Mulligan). Briefly, $1\times10^6$ cells were plated with $1\times10^8$ viral particles (MOI=100). After 24 hrs, cells were washed, and fresh medium was added. At 48 hr post-infection, the efficiency of infection was calculated based on percentage of GFP positive cells. 48 hr. later, cells were count and plate for the 3T3 passage and colony formation assays.

Western Analysis.

Western analysis was carried out as previously described (Cheng et al., 2003). Antibodies: anti-p19 (Abcam, ab80); anti-p16 (Santa Cruz); anti-SIRT1 (Upstate); anti-□-tubulin (Sigma); anti-p53 (CM-5, Novocastra); anti-p21 (Ab-4, Oncogene, Ab-4). p53 acetylation was assessed using PAbLys(Ac)379m antibody, as previously described (Cheng et al., 2003).

Soft Agar Assays.

Anchorage-independent growth was assessed by soft agar assays, as previously described (Dannenberg et al., 2000). Briefly, $2.5\times10^4$ cells were resuspended in 2 ml 0.4% low melting point agarose (Sigma) in DMEM with 13% serum, and seeded into 6-well plates coated with 1% low melting point agarose in DMEM with 10% serum. Foci were scored and photographed after 14 days.

Cell Cycle Analysis.

BrdU incorporation was assayed with anti-BrdU antibodies (BD Pharmingen) according to the manufacturer's instructions. Briefly, $5\times10^5$ cells were pulsed with BrdU for 4 hours, harvested, stained with FITC-conjugated anti-BrdU antibodies and propidium iodide, and cell-cycle profiles analyzed by flow cytometry.

REFERENCES

All references cited herein are hereby incorporated by reference.

Astrom, S. U., Cline, T. W., and Rine, J. (2003). The *Drosophila melanogaster* sir2(+) Gene Is Nonessential and Has Only Minor Effects on Position-Effect Variegation. Genetics 163, 931-937.

Bardeesy, N., Sinha, M., Hezel, A. F., Signoretti, S., Hathaway, N. A., Sharpless, N. E., Loda, M., Carrasco, D. R., and DePinho, R. A. (2002). Loss of the Lkb1 tumour suppressor provokes intestinal polyposis but resistance to transformation. Nature 419, 162-167.

Ben-Porath, I., and Weinberg, R. A. (2004). When cells get stressed: an integrative view of cellular senescence. J Clin Invest 113, 8-13.

Blander, G., and Guarente, L. (2004). The sir2 family of protein deacetylases. Annu Rev Biochem 73, 417-435.

Brown, J. P., Wei, W., and Sedivy, J. M. (1997). Bypass of senescence after disruption of p21CIP1/WAF1 gene in normal diploid human fibroblasts. Science 277, 831-834.

Brunet, A., Sweeney, L. B., Sturgill, J. F., Chua, K. F., Greer, P. L., Lin, Y., Tran, H., Ross, S. E., Mostoslavsky, R., Cohen, H. Y., et al. (2004). Stress-dependent regulation of FOXO transcription factors by the SIRT1 deacetylase. Science 303, 2011-2015.

Busuttil, R. A., Dolle, M., Campisi, J., and Vijg, J. (2004). Genomic Instability, Aging, and Cellular Senescence. Ann N Y Acad Sci 1019, 245-255.

Campisi, J. (1997). Aging and cancer: the double-edged sword of replicative senescence. J Am Geriatr Soc 45, 482-488.

Campisi, J. (2000). Cancer, aging and cellular senescence. In Vivo 14, 183-188.

Carlson, H., Ota, S., Song, Y., Chen, Y., and Hurlin, P. J. (2002). Tbx3 impinges on the p53 pathway to suppress apoptosis, facilitate cell transformation and block myogenic differentiation. Oncogene 21, 3827-3835.

Chen, Q., Fischer, A., Reagan, J. D., Yan, L. J., and Ames, B. N. (1995). Oxidative DNA damage and senescence of human diploid fibroblast cells. Proc Natl Acad Sci USA 92, 4337-4341.

Cheng, H., Mostoslavsky, R., Saito, S. i., Manis, J. P., Gu, Y., Patel, P., Bronson, R., Appella, E., Alt, F. W., and Chua, a. K. F. (2003). Developmental defects and p53 hyperacetylation in Sir2 homolog (SIRT1)-deficient mice. Proceedings of the National Academy of Sciences 100, 10794-10799.

Cohen, H. Y., Lavu, S., Bitterman, K. J., Hekking, B., Imahiyerobo, T. A., Miller, C., Frye, R., Ploegh, H., Kessler, B. M., and Sinclair, D. A. (2004). Acetylation of the C terminus of Ku70 by CBP and PCAF controls Bax-mediated apoptosis. Mol Cell 13, 627-638.

Daitoku, H., Hatta, M., Matsuzaki, H., Aratani, S., Ohshima, T., Miyagishi, M., Nakajima, T., and Fukamizu, A. (2004). Silent information regulator 2 potentiates Foxo1-mediated transcription through its deacetylase activity. Proc Natl Acad Sci USA 101, 10042-10047.

Dannenberg, J. H., van Rossum, A., Schuijff, L., and te Riele, H. (2000). Ablation of the retinoblastoma gene family deregulates G(1) control causing immortalization and increased cell turnover under growth-restricting conditions. Genes Dev 14, 3051-3064.

Finkel, T., and Holbrook, N. J. (2000). Oxidants, oxidative stress and the biology of ageing. Nature 408, 239-247.

Frye, R. A. (2000). Phylogenetic classification of prokaryotic and eukaryotic Sir2-like proteins. Biochem Biophys Res Commun 273, 793-798.

Hayflick, L., and Moorhead, P. S. (1961). The serial cultivation of human diploid cell strains. Exp Cell Res 25, 585-621.

Irani, K., Xia, Y., Zweier, J. L., Sollott, S. J., Der, C. J., Fearon, E. R., Sundaresan, M., Finkel, T., and Goldschmidt-Clermont, P. J. (1997). Mitogenic signaling mediated by oxidants in Ras-transformed fibroblasts. Science 275, 1649-1652.

Itahana, K., Campisi, J., and Dimri, G. P. (2004). Mechanisms of cellular senescence in human and mouse cells. Biogerontology 5, 1-10.

Iwama, A., Oguro, H., Negishi, M., Kato, Y., Morita, Y., Tsukui, H., Ema, H., Kamijo, T., Katoh-Fukui, Y., Koseki, H., et al. (2004). Enhanced self-renewal of hematopoietic stem cells mediated by the polycomb gene product Bmi-1. Immunity 21, 843-851.

Jacobs, J. J., Keblusek, P., Robanus-Maandag, E., Kristel, P., Lingbeek, M., Nederlof, P. M., van Welsem, T., van de Vijver, M. J., Koh, E. Y., Daley, G. Q., and van Lohuizen, M. (2000). Senescence bypass screen identifies TBX2, which represses Cdkn2a (p19(ARF)) and is amplified in a subset of human breast cancers. Nat Genet 26, 291-299.

Jacobs, J. J., Kieboom, K., Marino, S., DePinho, R. A., and van Lohuizen, M. (1999). The oncogene and Polycomb-group gene bmi-1 regulates cell proliferation and senescence through the ink4a locus. Nature 397, 164-168.

Kaeberlein, M., McVey, M., and Guarente, L. (1999). The SIR2/3/4 complex and SIR2 alone promote longevity in Saccharomyces cerevisiae by two different mechanisms. Genes Dev 13, 2570-2580.

Kamijo, T., Zindy, F., Roussel, M. F., Quelle, D. E., Downing, J. R., Ashmun, R. A., Grosveld, G., and Sherr, C. J. (1997). Tumor suppression at the mouse INK4a locus mediated by the alternative reading frame product p19ARF. Cell 91, 649-659.

Kaushal, D., Contos, J. J., Treuner, K., Yang, A. H., Kingsbury, M. A., Rehen, S. K., McConnell, M. J., Okabe, M., Barlow, C., and Chun, J. (2003). Alteration of gene expression by chromosome loss in the postnatal mouse brain. J Neurosci 23, 5599-5606.

Kranc, K. R., Bamforth, S. D., Braganca, J., Norbury, C., van Lohuizen, M., and Bhattacharya, S. (2003). Transcriptional coactivator Cited2 induces Bmi1 and Mel18 and controls fibroblast proliferation via Ink4a/ARF. Mol Cell Biol 23, 7658-7666.

Krtolica, A., and Campisi, J. (2002). Cancer and aging: a model for the cancer promoting effects of the aging stroma. Int J Biochem Cell Biol 34, 1401-1414.

Kuo, M. L., den Besten, W., and Sherr, C. J. (2004). N-Terminal polyubiquitination of the ARF tumor suppressor, a natural lysine-less protein. Cell Cycle 3, 1367-1369.

Kurokawa, K., Tanaka, T., and Kato, J. (1999). p19ARF prevents G1 cyclin-dependent kinase activation by interacting with MDM2 and activating p53 in mouse fibroblasts. Oncogene 18, 2718-2727.

Langley, E., Pearson, M., Faretta, M., Bauer, U. M., Frye, R. A., Minucci, S., Pelicci, P. G., and Kouzarides, T. (2002). Human SIR2 deacetylates p53 and antagonizes PML/p53-induced cellular senescence. Embo J 21, 2383-2396.

Lee, A. C., Fenster, B. E., Ito, H., Takeda, K., Bae, N. S., Hirai, T., Yu, Z. X., Ferrans, V. J., Howard, B. H., and Finkel, T. (1999). Ras proteins induce senescence by altering the intracellular levels of reactive oxygen species. J Biol Chem 274, 7936-7940.

Luo, J., Nikolaev, A. Y., Imai, S., Chen, D., Su, F., Shiloh, A., Guarente, L., and Gu, W. (2001). Negative control of p53 by Sir2alpha promotes cell survival under stress. Cell 107, 137-148.

Maeda, T., Hobbs, R. M., Merghoub, T., Guernah, I., Zelent, A., Cordon-Cardo, C., Teruya-Feldstein, J., and Pandolfi, P. P. (2005). Role of the proto-oncogene Pokemon in cellular transformation and ARF repression. Nature 433, 278-285.

Mazars, G. R., and Jat, P. S. (1997). Expression of p24, a novel p21Waf1/Cip1/Sdi1-related protein, correlates with measurement of the finite proliferative potential of rodent embryo fibroblasts. Proc Natl Acad Sci USA 94, 151-156.

McBurney, M. W., Yang, X., Jardine, K., Hixon, M., Boekelheide, K., Webb, J. R., Lansdorp, P. M., and Lemieux, M. (2003). The mammalian SIR2alpha protein has a role in embryogenesis and gametogenesis. Mol Cell Biol 23, 38-54.

Michishita, E., Horikawa, I., Saito, S., Padilla-Nash, H., Kioi, M., Aprelikova, O., Gadisetti, C., Sedelnikova, O. A., Bonner, W. M., Ried, T., et al. (2005). Extension of human cell lifespan by decreased expression of SIRT1, a human homolog of yeast longevity protein Sir2. Submitted.

Mikula, M., Fuchs, E., Huber, H., Beug, H., Schulte-Hermann, R., and Mikulits, W. (2004). Immortalized p19ARF null hepatocytes restore liver injury and generate hepatic progenitors after transplantation. Hepatology 39, 628-634.

Motta, M. C., Divecha, N., Lemieux, M., Kamel, C., Chen, D., Gu, W., Bultsma, Y., McBurney, M., and Guarente, L. (2004). Mammalian SIRT1 Represses Forkhead Transcription Factors. Cell 116, 551-563.

Nemoto, S., and Finkel, T. (2002). Redox regulation of forkhead proteins through a p66shc-dependent signaling pathway. Science 295, 2450-2452.

Oren, M. (2003). Decision making by p53: life, death and cancer. Cell Death Differ 10, 431-442.

Palmero, I., Pantoja, C., and Serrano, M. (1998). p19ARF links the tumour suppressor p53 to Ras. Nature 395, 125-126.

Palmero, I., and Serrano, M. (2001). Induction of senescence by oncogenic Ras. Methods Enzymol 333, 247-256.

Pantoja, C., and Serrano, M. (1999). Murine fibroblasts lacking p21 undergo senescence and are resistant to transformation by oncogenic Ras. Oncogene 18, 4974-4982.

Parrinello, S., Samper, E., Krtolica, A., Goldstein, J., Melov, S., and Campisi, J. (2003). Oxygen sensitivity severely limits the replicative lifespan of murine fibroblasts. Nat Cell Biol 5, 741-747.

Pearson, M., Carbone, R., Sebastiani, C., Cioce, M., Fagioli, M., Saito, S., Higashimoto, Y., Appella, E., Minucci, S., Pandolfi, P. P., and Pelicci, P. G. (2000). PML regulates p53 acetylation and premature senescence induced by oncogenic Ras. Nature 406, 207-210.

Pomerantz, J., Schreiber-Agus, N., Liegeois, N. J., Silverman, A., Alland, L., Chin, L., Potes, J., Chen, K., Orlow, I., Lee, H. W., et al. (1998). The Ink4a tumor suppressor gene product, p19Arf, interacts with MDM2 and neutralizes MDM2's inhibition of p53. Cell 92, 713-723.

Prives, C., and Manley, J. L. (2001). Why is p53 acetylated? Cell 107, 815-818.

Quelle, D. E., Zindy, F., Ashmun, R. A., and Sherr, C. J. (1995). Alternative reading frames of the INK4a tumor suppressor gene encode two unrelated proteins capable of inducing cell cycle arrest. Cell 83, 993-1000.

Robles, S. J., and Adami, G. R. (1998). Agents that cause DNA double strand breaks lead to p16INK4a enrichment and the premature senescence of normal fibroblasts. Oncogene 16, 1113-1123.

Rogina, B., and Helfand, S. L. (2004). Sir2 mediates longevity in the fly through a pathway related to calorie restriction. Proc Natl Acad Sci USA 101, 15998-16003.

Sage, J., Mulligan, G. J., Attardi, L. D., Miller, A., Chen, S., Williams, B., Theodorou, E., and Jacks, T. (2000). Targeted disruption of the three Rb-related genes leads to loss of G(1) control and immortalization. Genes Dev 14, 3037-3050.

Sedelnikova, O. A., Horikawa, I., Zimonjic, D. B., Popescu, N. C., Bonner, W. M., and Barrett, J. C. (2004). Senescing human cells and ageing mice accumulate DNA lesions with unrepairable double-strand breaks. Nat Cell Biol 6, 168-170.

Serrano, M., Lin, A. W., McCurrach, M. E., Beach, D., and Lowe, S. W. (1997). Oncogenic ras provokes premature cell senescence associated with accumulation of p53 and p16INK4a. Cell 88, 593-602.

Sherr, C. J., and DePinho, R. A. (2000). Cellular senescence: mitotic clock or culture shock? Cell 102, 407-410.

Sinclair, D. A., and Guarente, L. (1997). Extrachromosomal rDNA circles—a cause of aging in yeast. Cell 91, 1033-1042.

Stott, F. J., Bates, S., James, M. C., McConnell, B. B., Starborg, M., Brookes, S., Palmero, I., Ryan, K., Hara, E., Vousden, K. H., and Peters, G. (1998). The alternative product from the human CDKN2A locus, p14(ARF), participates in a regulatory feedback loop with p53 and MDM2. Embo J 17, 5001-5014.

Sundaresan, M., Yu, Z. X., Ferrans, V. J., Sulciner, D. J., Gutkind, J. S., Irani, K., Goldschmidt-Clermont, P. J., and Finkel, T. (1996). Regulation of reactive-oxygen-species generation in fibroblasts by Rac1. Biochem J 318 (Pt 2), 379-382.

Tissenbaum, H. A., and Guarente, L. (2001). Increased dosage of a sir-2 gene extends lifespan in Caenorhabditis elegans. Nature 410, 227-230.

Todaro, G. J., and Green, H. (1963). Quantitative studies of the growth of mouse embryo cells in culture and their development into established lines. J Cell Biol 17, 299-313.

Van Der Horst, A., Tertoolen, L. G., De Vries-Smits, L. M., Frye, R. A., Medema, R. H., and Burgering, B. M. (2004). FOXO4 Is Acetylated upon Peroxide Stress and Deacetylated by the Longevity Protein hSir2SIRT1. J Biol Chem 279, 28873-28879.

Vaziri, H., Dessain, S. K., Ng Eaton, E., Imnai, S. I., Frye, R. A., Pandita, T. K., Guarente, L., and Weinberg, R. A. (2001). hSIR2(SIRT1) functions as an NAD-dependent p53 deacetylase. Cell 107, 149-159.

Vousden, K. H., and Lu, X. (2002). Live or let die: the cell's response to p53. Nat Rev Cancer 2, 594-604.

Wei, W., Hemmer, R. M., and Sedivy, J. M. (2001). Role of p14(ARF) in replicative and induced senescence of human fibroblasts. Mol Cell Biol 21, 6748-6757.

Wood, J. G., Rogina, B., Lavu, S., Howitz, K., Helfand, S. L., Tatar, M., and Sinclair, D. (2004). Sirtuin activators mimic caloric restriction and delay ageing in metazoans. Nature.

Wright, W. E., and Shay, J. W. (2000). Telomere dynamics in cancer progression and prevention: fundamental differences in human and mouse telomere biology. Nat Med 6, 849-851.

Zhang, Y., Xiong, Y., and Yarbrough, W. G. (1998). ARF promotes MDM2 degradation and stabilizes p53: ARF-INK4a locus deletion impairs both the Rb and p53 tumor suppression pathways. Cell 92, 725-734.

Zindy, F., Eischen, C. M., Randle, D. H., Kamijo, T., Cleveland, J. L., Sherr, C. J., and Roussel, M. F. (1998). Myc signaling via the ARF tumor suppressor regulates p53-dependent apoptosis and immortalization. Genes Dev 12, 2424-2433.

Zindy, F., Quelle, D. E., Roussel, M. F., and Sherr, C. J. (1997). Expression of the p16INK4a tumor suppressor versus other INK4 family members during mouse development and aging. Oncogene 15, 203-211.

---

We claim:

1. A method of overcoming replicative senescence of mammalian cells, comprising culturing the cells in the presence of an active agent or compound that inhibits the expression of SIRT1, wherein the agent or compound is a RNA interfering agent and/or a peptide nucleic acid (PNA); and wherein said cultured cells are resistant to replicative senescence.

2. The method of claim 1, wherein the RNA interfering agent is a double stranded, short interfering RNA (siRNA).

3. The method of claim 2, wherein the siRNA is about 15 to about 28 nucleotides in length.

4. The method of claim 2, wherein the siRNA is about 19 to about 25 nucleotides in length.

5. The method of claim 2, wherein the siRNA is about 21 nucleotides in length.

6. The method of claim 2, wherein said siRNA is double-stranded and comprises a 3' overhand on each strand.

7. The method of claim 2, wherein said siRNA inhibits SIRT1 by transcriptional silencing.

8. The method of claim 1, wherein the cells are stem cells.

9. The method of claim 8, wherein the cells are somatic stem cells.

10. The method of claim 9, wherein the somatic stem cells are neuronal stem cells.

11. The method of claim 1, wherein the cells are human cells.

12. The method of claim 1, wherein the cells are murine cells.

13. The method of claim 1, wherein the cells in which SIRT1 is inhibited are further cultured to undergo at least one mitotic cell division.

14. The method of claim 1, wherein the cells in which SIRT1 is inhibited are further cultured to undergo at least ten mitotic cell divisions.

15. The method of claim 1, wherein the cultured cells are capable of self-renewal and expansion in culture, and have the potential to differentiate into cells of other phenotypes.

* * * * *

SEQUENCE LISTING

```
<160> NUMBER OF SEQ ID NOS: 4

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 ttaggg                                                                    6

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ttagggttag ggttaggg                                                      18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (3)..(21)
<223> OTHER INFORMATION: a, c, g, t, unknown or other

<400> SEQUENCE: 3
aannnnnnnn nnnnnnnnnn ntt                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: a, c, g, t, unknown or other
<220> FEATURE:
<221> NAME/KEY: modified_base
<222> LOCATION: (3)..(23)
<223> OTHER INFORMATION: a, c, g, t, unknown or other

<400> SEQUENCE: 4
nannnnnnnn nnnnnnnnnn nnn                                              23
```